(12) United States Patent
Hou et al.

(10) Patent No.: US 11,987,793 B2
(45) Date of Patent: *May 21, 2024

(54) COMPOSITIONS AND METHODS FOR PREVENTION OF BLADDER FIBROSIS

(71) Applicants: Washington University, St. Louis, MO (US); Wisconsin Alumni Research Foundation, Madison, WI (US)

(72) Inventors: Jianghui Hou, St. Louis, MO (US); Dale Bjorling, Madison, WI (US); Zunyi Wang, Madison, WI (US)

(73) Assignees: Washington University, St. Louis, MO (US); Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/306,929

(22) Filed: May 3, 2021

(65) Prior Publication Data

US 2021/0340538 A1 Nov. 4, 2021

Related U.S. Application Data

(60) Provisional application No. 63/019,425, filed on May 3, 2020.

(51) Int. Cl.
*C12N 15/113* (2010.01)
*A61K 47/54* (2017.01)
*A61K 47/59* (2017.01)

(52) U.S. Cl.
CPC .......... *C12N 15/113* (2013.01); *A61K 47/549* (2017.08); *A61K 47/554* (2017.08);
(Continued)

(58) Field of Classification Search
CPC ............ C12N 15/113; C12N 2310/141; C12N 2310/321
See application file for complete search history.

(56) References Cited

U.S. PATENT DOCUMENTS

| 9,376,681 | B2 | 6/2016 | Montgomery et al. |
| 10,472,631 | B2 | 11/2019 | Gilchrist et al. |
| 11,021,712 | B1 * | 6/2021 | Hou ..................... C12N 15/113 |

OTHER PUBLICATIONS

Kim et al. (Int Neurourol J., 2021 vol. 25:S3-S7).*

(Continued)

*Primary Examiner* — Terra C Gibbs

(57) ABSTRACT

A composition for the treatment of bladder fibrosis in a patient in need that includes a miR-29 mimic is disclosed. The miR-29 mimic may include a working RNA strand with the nucleotide sequence UAGCACCAUCUGAAAUCG-GUUUU (SEQ ID NO 4) and a passenger RNA strand comprising the nucleotide sequence: AACCGAUUUC-uuuUGGUGCUAUU (SEQ ID NO 5). The passenger RNA strand includes a 2'-O-methylation modification to increase stability. Cholesterol is conjugated to the 3'-end of the passenger RNA strand to enhance cellular uptake. The composition may further include a carrier molecule including, but not limited to, branched polyethylenimine at an N/P ratio of 0.8, where N denotes the nitrogens of the polyethylenimine and P denotes the phosphate groups of the working and passenger RNA strands. In some aspects, the composition may be an injectable composition that includes a polyplex dissolved in a 0.5% glucose solution, where the polyplex is formed from the working and passenger RNA strands and the carrier molecule.

16 Claims, 16 Drawing Sheets

Specification includes a Sequence Listing.

(52) U.S. Cl.
CPC ........ *A61K 47/59* (2017.08); *C12N 2310/141* (2013.01); *C12N 2310/321* (2013.01); *C12N 2310/3515* (2013.01)

(56) References Cited

OTHER PUBLICATIONS

Massari et al. (Cancer Treatment Reviews, 2016 vol. 45:45-57).*
Sun, J. et al. (2019) MicroRNA-29b Mediates Lung Mesenchymal-Epithelial Transition and Prevents Lung Fibrosis in the Silicosis Model. Molecular Therapy: Nucleic Acids, vol. 14, pp. 20-31.
Monaghan, M. et al. (2011) A ligand enhanced dendritic PEGylated poly (2-(dimethylamino) ethyl diacrylate) as a vehicle of microRNA. Drug Del Trans Res, vol. 2, pp. 406-414.
Bjorling, D. et al. (2019) MicroRNA-29A Inhibits Signaling for Bladder Fibrosis Induced by Bladder Outlet Obstruction. The Journal of Urology, vol. 201, No. 4S, Supplement PD14-09, pp. e234.

* cited by examiner

SEQUENCE LISTING

<160> NUMBER OF SEQ ID NOS: 5

<210> SEQ ID NO 1
<211> LENGTH: 22
<212> TYPE: RNA
<213> ORGANISM: Artificial Sequence
<220> FEATURE:
<223> OTHER INFORMATION: Synthetic sequence

<400> SEQUENCE: 1
uagcaccauc ugaaaucggu ua                                    22

```
<210> SEQ ID NO 2
<211> LENGTH: 23
<212> TYPE: RNA
<213> ORGANISM: Artificial Sequence
<220> FEATURE:
<223> OTHER INFORMATION: Synthetic sequence

<400> SEQUENCE: 2
uagcaccauu ugaaaucagu guu                                    23

<210> SEQ ID NO 3
<211> LENGTH: 22
<212> TYPE: RNA
<213> ORGANISM: Artificial Sequence
<220> FEATURE:
<223> OTHER INFORMATION: Synthetic sequence

<400> SEQUENCE: 3
uagcaccauu ugaaaucggu ua                                     22

<210> SEQ ID NO 4
<211> LENGTH: 23
<212> TYPE: RNA
<213> ORGANISM: Artificial Sequence
<220> FEATURE:
<223> OTHER INFORMATION: Synthetic sequence

<400> SEQUENCE: 4
uagcaccauc ugaaaucggu uuu                                    23

<210> SEQ ID NO 5
<211> LENGTH: 23
<212> TYPE: RNA
<213> ORGANISM: Artificial Sequence
<220> FEATURE:
<223> OTHER INFORMATION: Synthetic sequence

<400> SEQUENCE: 5
aaccgauuuc uuuuggugcu auu                                    23
```

COMPOSITIONS AND METHODS FOR PREVENTION OF BLADDER FIBROSIS

CROSS-REFERENCE TO RELATED APPLICATIONS

This application claims the benefit of priority from U.S. Provisional Application Ser. No. 63/019,425 filed on May 3, 2020, the content of which is incorporated herein by reference in its entirety.

STATEMENT REGARDING FEDERALLY SPONSORED RESEARCH OR DEVELOPMENT

This invention was made with government support under DK118145, DK104310, and DK084059 awarded by the National Institutes of Health. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE DISCLOSURE

The present disclosure generally relates to compositions and methods for the prevention of bladder fibrosis.

BACKGROUND OF THE DISCLOSURE

Bladder fibrosis is relatively common in patients subsequent to partial bladder outlet obstruction (BOO), neurogenic disorders, radiation therapy of the lower abdomen, chronic inflammation, or as a natural effect of aging. Furthermore, fibrosis often persists beyond resolution of the inciting factor(s), particularly in pediatric patients, and lack of effective strategies to reduce bladder fibrosis remains a significant therapeutic gap.

A majority of benign bladder disorders are accompanied by fibrosis of the bladder wall and that fibrosis ultimately results in decreased compliance and increased stiffness of the bladder. These structural changes increase urine retention during voiding, creating an urgent need for more effective strategies to decrease deposition of extracellular matrix within the bladder wall while minimizing undesirable side-effects.

MicroRNAs are single-stranded, non-coding RNA molecules nucleotides in length generated from endogenous hairpin-shaped transcripts. MicroRNAs bind to specific target mRNAs, and either repress translation of mRNA or cause destabilization of mRNA thereby accelerating mRNA degradation. The microRNA-29 (miR-29) family suppresses translation of genes that promote expression of many components of the extracellular matrix, including 20 isoforms of collagen, laminin γ1, fibrillin 1, elastin, and integrin β1. Compelling evidence has been reported that miR-29 is decreased in bladders of patients with BOO and in rats with experimentally-created BOO.

MicroRNAs (miRNA) are short (19-25 nucleotides), non-coding RNA sequences that bind to the 3' untranslated region of various messenger RNA (mRNA), accelerating mRNA degradation or preventing translation of the encoded protein. MicroRNA-29 or miR-29 suppresses translation of genes related to extracellular matrix (ECM) formation, particularly various collagens, collagen cross-linking elements, and enzymes that regulate post-translational modification of the ECM proteins. Dysregulation of ECM formation results in fibrosis. A recent study comprehensively investigated miRNA abundance and signaling in bladder biopsies from patients with bladder outlet obstruction and found significant increases or decreases in multiple miRNAs, but specifically reported a decrease in miR-29.

Most studies of miR-29 have focused on its role in pathogenesis of fibrosis in the lung, liver, and kidney. Lack of miR-29 alone fails to induce fibrosis in these organs, but bladder fibrosis and dysfunction in mice deficient for miR-29a/b1 (knockout or KO mice) has been observed in the absence of fibrosis-inducing stimuli, strongly suggesting that miR-29a/b1 is necessary to maintain homeostasis in the bladder. Furthermore, therapeutic strategies that increase miR-29 prevent or reverse experimentally-induced fibrosis in several organs, strongly supporting the concept that similar results can be achieved in the bladder.

SUMMARY OF THE DISCLOSURE

Among the various aspects of the present disclosure is the provision of a composition for the treatment of bladder fibrosis in a patient in need that includes a miR-29 mimic. The miR-29 mimic may include a working RNA strand with the nucleotide sequence UAGCACCAUCUGAAAUCG-GUUUU (SEQ ID NO 4) and a passenger RNA strand comprising the nucleotide sequence: AACCGAUUUC-uuuUGGUGCUAUU (SEQ ID NO 5). The passenger RNA strand includes a 2'-O-methylation modification to increase stability. Cholesterol is conjugated to the 3'-end of the passenger RNA strand to enhance cellular uptake. The composition may further include a carrier molecule including, but not limited to, branched polyethylenimine at an N/P ratio of 0.8, where N denotes the nitrogens of the polyethylenimine and P denotes the phosphate groups of the working and passenger RNA strands. In some aspects, the composition may be an injectable composition that includes a polyplex dissolved in a 0.5% glucose solution, where the polyplex is formed from the working and passenger RNA strands and the carrier molecule.

Other objects and features will be in part apparent and in part pointed out hereinafter.

Figure 1:
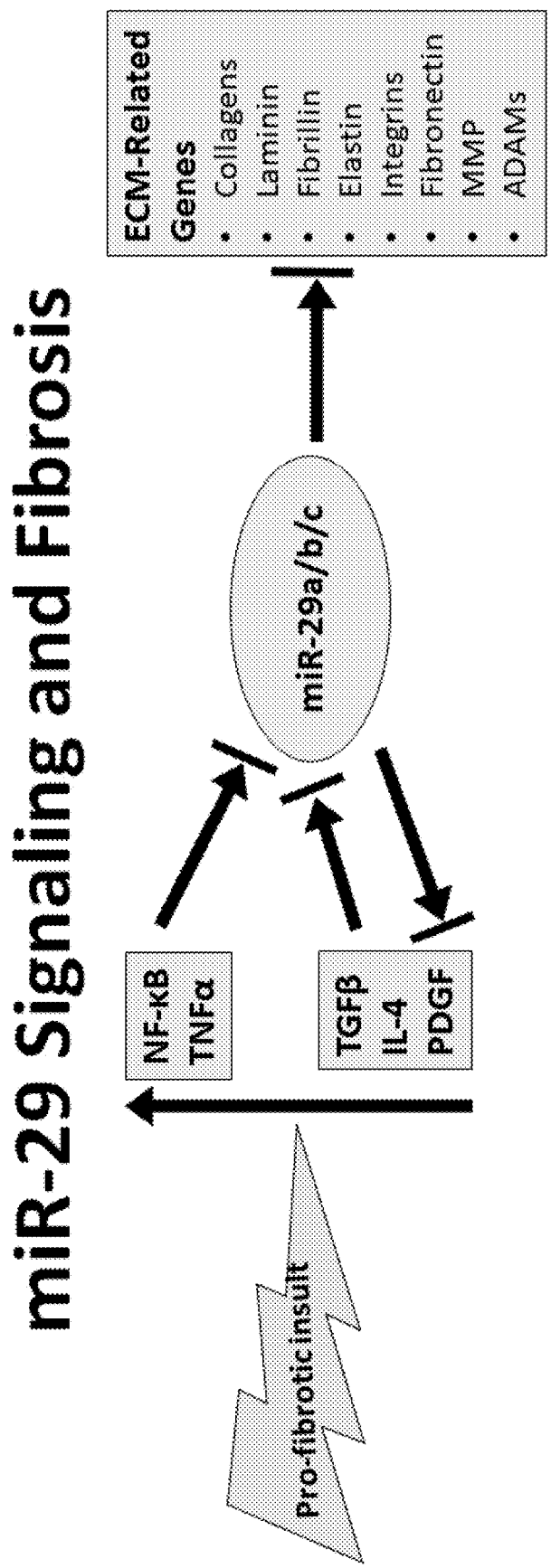
FIG. 1 is a schematic diagram illustrating miR-29 signaling in fibrosis. miR-29 acts constitutively to inhibit translation of mRNA coding for extracellular matrix proteins (ECM), including MMP (matrix metalloproteinases) and ADAMs (a disintegrin and metalloproteinase) that mediate restructuring of the ECM. Tissue damage activates pro-fibrotic pathways that inhibit the abundance and function of miR-29. miR-29 acts in a reciprocal manner to inhibit function of a subset of these cytokines, particularly TGFβ and its signaling pathway.

Those of skill in the art will understand that the drawings, described below, are for illustrative purposes only. The drawings are not intended to limit the scope of the present teachings in any way.

DETAILED DESCRIPTION OF THE INVENTION

The present disclosure is based, at least in part, on the discovery that administration of various forms of miR-29 including, but not limited to miR-29a (SEQ ID NO:1), miR-29b (SEQ ID NO:2), miR-29c (SEQ ID NO:3) and miR-29 mimic (SEQ ID NOS:4-5) reverses bladder fibrosis. As shown herein, the administration of a composition containing the miR-29 mimic reverses bladder fibrosis based upon gene expression program.

One aspect of the present disclosure provides a composition for the treatment of bladder fibrosis in a patient in need that includes a miR-29 mimic. The miR-29 mimic may include a working RNA strand with the nucleotide sequence UAGCACCAUCUGAAAUCGGUUUU (SEQ ID NO 4) and a passenger RNA strand comprising the nucleotide sequence: AACCGAUUUCuuuUGGUGCUAUU (SEQ ID NO 5). The passenger RNA strand includes a 2'-O-methylation modification to increase stability. Cholesterol is conjugated to the 3'-end of the passenger RNA strand to enhance cellular uptake. The composition may further include a carrier molecule including, but not limited to, branched polyethylenimine at an N/P ratio of 0.8, where N denotes the nitrogens of the polyethylenimine and P denotes the phosphate groups of the working and passenger RNA strands. In some aspects, the composition may be an injectable composition that includes a polyplex dissolved in a 0.5% glucose solution, where the polyplex is formed from the working and passenger RNA strands and the carrier molecule.

Extracellular Matrix (ECM) Modulation Agents

As described herein, ECM-related gene expression has been implicated in various diseases, disorders, and conditions. As such, modulation of ECM-related gene expression (e.g., modulation of genes related to extracellular matrix (ECM) formation, particularly various collagens, collagen cross-linking elements, and enzymes that regulate post-translational modification of the ECM proteins) can be used for treatment of such conditions. An ECM modulation agent can modulate ECM-related gene response or induce or inhibit ECM formation. ECM-related gene modulation can comprise modulating the expression of genes related to extracellular matrix (ECM) formation on cells, modulating the quantity of cells that express genes related to extracellular matrix (ECM) formation, or modulating the quality of the ECM-forming cells.

ECM modulation agents can be any composition or method that can modulate expression of ECM-related gene on cells (e.g., modulation of genes related to extracellular matrix (ECM) formation, particularly various collagens, collagen cross-linking elements, and enzymes that regulate post-translational modification of the ECM proteins). For example, an ECM modulation agent can be an activator, an inhibitor, an agonist, or an antagonist. As another example, the ECM modulation can be the result of gene editing.

ECM Formation Signal Reduction, Elimination, or Inhibition by microRNAs

As described herein, an ECM modulation agent can be used for use in the prevention or reversal of bladder fibrosis. An ECM modulation agent can be used to enhance/increase microRNA-29 (miR-29) signals. For example, an ECM modulation agent can be exogenous miR-29, including, but not limited to an miR-29 mimic.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling or cloning. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position+1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A construct of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m=81.5°$ C.$+16.6(\log_{10}[Na^+])+0.41$ (fraction G/C content)$-0.63$ (% formamide)$-(600/l)$. Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

| Conservative Substitutions I | |
|---|---|
| Side Chain Characteristic | Amino Acid |
| Aliphatic Non-polar | G A P I L V |
| Polar-uncharged | C S T M N Q |
| Polar-charged | D E K R |
| Aromatic | H F W Y |
| Other | N Q D E |

| Conservative Substitutions II | |
|---|---|
| Side Chain Characteristic | Amino Acid |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

| Conservative Substitutions III | |
|---|---|
| Original Residue | Exemplary Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met(M) | Leu, Phe, Ile |
| Phe (F) | Leu, Val, Ile, Ala |
| Pro (P) | Gly |
| Ser (S) | Thr |
| Thr (T) | Ser |
| Trp(W) | Tyr, Phe |
| Tyr (Y) | Trp, Phe, Tur, Ser |
| Val (V) | Ile, Leu, Met, Phe, Ala |

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides (ASOs), protein aptamers, nucleotide aptamers, and RNA interference (RNAi) (e.g., small interfering RNAs (siRNA), short hairpin RNA (shRNA), and micro RNAs (miRNA) (see e.g., Rinaldi and Wood (2017) Nature Reviews Neurology 14, describing ASO therapies; Fanning and Symonds (2006) Handb Exp Pharmacol. 173, 289-303G, describing hammerhead ribozymes and small hairpin RNA; Helene, et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Genome Editing

As described herein, miR-29 signals can be modulated (e.g., enhanced) using genome editing. Processes for genome editing are well known; see e.g. Aldi 2018 Nature Communications 9(1911). Except as otherwise noted herein, therefore, the process of the present disclosure can be carried out in accordance with such processes.

For example, genome editing can comprise CRISPR/Cas9, CRISPR-Cpf1, TALEN, or ZNFs. Adequate blockage of ECM-related gene expression by genome editing to enhance miRNA-29 production can result in protection from bladder fibrosis.

As an example, clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a $(N)_{20}$NGG target DNA sequence). This results in a double-strand break three nucleotides upstream of the NGG motif. The double strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, genomic editing, for example, using CRISPR/Cas systems could be useful tools for therapeutic applications for reduced ECM formation to target cells by the enhancement of miR-29 signals.

For example, the methods as described herein can comprise a method for altering a target polynucleotide sequence in a cell comprising contacting the polynucleotide sequence with a clustered regularly interspaced short palindromic repeats-associated (Cas) protein.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating, preventing, or reversing bladder fibrosis in a subject in need of administration of a therapeutically effective amount of miRNA-29 or an miRNA-29 mimic, so as to prevent, reduce, or reverse of bladder fibrosis.

Methods described herein are generally performed on a subject in need thereof. A subject in need of the therapeutic methods described herein can be a subject having, diagnosed with, suspected of having, or at risk for developing bladder fibrosis. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of miRNA-29 or an miRNA-29 mimic is, for example, an amount that would cause the desired therapeutic effect in a subject while minimizing undesired side effects. In various embodiments, an effective amount of miRNA-29 or an miRNA-29 mimic described herein can substantially inhibit bladder fibrosis, slow the progress of bladder fibrosis, or limit the development of bladder fibrosis.

According to the methods described herein, administration can be parenteral, pulmonary, oral, topical, intradermal, intramuscular, intraperitoneal, intravenous, intratumoral, intrathecal, intracranial, intracerebroventricular, subcutaneous, intranasal, epidural, ophthalmic, buccal, or rectal administration.

When used in the treatments described herein, a therapeutically effective amount of miRNA-29 or an miRNA-29 mimic can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to prevent, reduce, or reverse bladder fibrosis.

The amount of a composition described herein that can be combined with a pharmaceutically acceptable carrier to produce a single dosage form will vary depending upon the subject or host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4$^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing, reversing, or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of miRNA-29 or an miRNA-29 mimic can occur as a single event or over a time course of treatment. For example, miRNA-29 or an miRNA-29 mimic can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for prevention, reduction, or reversal of bladder fibrosis.

An miRNA-29 or an miRNA-29 mimic can be administered simultaneously or sequentially with another agent, such as an antibiotic, an anti-inflammatory, or another agent. For example, an miRNA-29 or an miRNA-29 mimic can be administered simultaneously with another agent, such as an antibiotic or an anti-inflammatory. Simultaneous administration can occur through administration of separate compositions, each containing one or more of an miRNA-29 or an miRNA-29 mimic, an antibiotic, an anti-inflammatory, or another agent. Simultaneous administration can occur through administration of one composition containing two or more of an miRNA-29 or an miRNA-29 mimic, an antibiotic, an anti-inflammatory, or another agent. An miRNA-29 or an miRNA-29 mimic can be administered sequentially with an antibiotic, an anti-inflammatory, or another agent. For example, an miRNA-29 or an miRNA-29 mimic can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD)

with relatively fewer features (e.g., less than about 3 hydrogen donors and/or less than about 6 hydrogen acceptors; hydrophobicity character xlogP of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to compositions containing miRNA-29 or miRNA-29 mimics as described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium or video. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Role of Mir-29A/B1 in Development of Bladder Fibrosis and Impaired Bladder Function To characterize the role of decreased miR-29a/b1 function in development of bladder fibrosis and impaired bladder function, to delineate the role of tissue-specific miR-29a/b1 function in the bladder, and to test whether increased miR-29a/b1 can prevent and reverse bladder fibrosis induced by partial bladder outlet obstruction, the following experiments are conducted.

Additional details regarding these experiments are provided in Appendix A, incorporated by reference herein in its entirety.

Specific Aims

Determine the necessity of miR-29a/b1 for normal bladder structure and function. Bladder structure and function will be assessed in mice deficient for miR-29a/b1. RNA sequencing (RNA-seq) will be performed to determine the effects of lack of miR29a/b1 on mRNA expression in the urothelium and detrusor.

Expression of miR-29a/b1 will be eliminated in a tissue-specific manner from the urothelium or detrusor of the bladder using a Cre-lox strategy entailing cross-breeding of mice with a floxed gene for miR-29a/b1 with mice that express Cre-recombinase under control of the promoter for either uroplakin 2 (Upk2; urothelium-specific) or Tbx18 (specific to the mesenchyma/smooth muscle of the lower urinary tract). Bladder structure and function will be evaluated to determine whether the location of miR-29a/b1 synthesis plays a critical role in effects on the bladder.

Partial bladder outlet obstruction (BOO) will be created in male and female mice. Bladders will be evaluated at time points up to 6 weeks after creation of BOO to determine abundance of miR-29a, mRNA for components of extracellular matrix, extracellular matrix proteins, and fibrosis. miR-29a/b1 expression will be increased in BOO mice in a bladder-specific manner (e.g., in urothelium and detrusor) delivered by adeno-associated viral 9 (AAV9) vectors. Alternatively, miR-29a oligonucleotide mimics will be administered systemically. Structure and function of bladders will be evaluated as previously described to assess the capacity of miR-29 to prevent or reverse BOO-induced fibrosis of the bladder wall.

Milestones

Determine whether miR-29a/b1 is critical for normal bladder structure and function.

Discriminate the effects of synthesis of miR-29a/b1 within the detrusor relative to those arising from synthesis of miR-29a/b1 by the urothelium.

Clarify the capacity of miR-29a/b1 to prevent or reverse structural and functional changes induced by BOO. Clinical trials are currently in progress to assess the efficacy of manipulation of various miRNAs to treat a variety of disorders, and clinically-applicable miRNA delivery alternatives exist to restore miR-29 expression within the bladder, underscoring the translational potential of this research.

Premise

Bladder fibrosis It was the consensus of a recently-convened panel of clinicians and scientists that bladder fibrosis is present in most benign bladder disorders and that there is an acute need for more effective strategies to prevent and treat bladder fibrosis.[31] Bladder fibrosis is relatively common in patients subsequent to partial bladder outlet obstruction (BOO),[32] neurogenic disorders,[33] radiation therapy of the lower abdomen,[34] chronic inflammation,[35] or as a natural effect of aging.[36] Furthermore, fibrosis often persists beyond resolution of the inciting factor(s), particularly in pediatric patients, and lack of effective strategies to reduce bladder fibrosis remains a significant therapeutic gap.[37] Directly targeting the canonical pro-fibrotic TGFβ/SMAD3 pathway disrupts the immune system and causes fatal multi-organ inflammation.[38-41] Inhibition of TGFβ by antibodies or pharmaceuticals prevented cardiac fibrosis in mice but was associated with unacceptably high mortality.[42,43]

Bladder physiology Bladder function is significantly impaired by fibrosis of the bladder wall. The presence of increased fibrous tissue and extracellular matrix within the bladder wall decreases compliance and contractility.[44-49] Experimental partial BOO in rats caused bladders to pass through predictable phases of inflammation and muscle hypertrophy, ending in deterioration characterized by fibrosis and decreased contractility and compliance,[32,50] a progression also described in BOO of human bladders.[51] These changes are very similar to those observed in heart failure due to pressure overload and resulting cardiac fibrosis.[52] Prolonged retention of urine associated with BOO results in increased extracellular matrix content comprised of collagen and elastic fibers, as well as causing degeneration of muscle fibers.[53-55] Bladder fibrosis is commonly observed in men with BOO associated with benign prostatic hyperplasia (BPH).[56,57] Bladder fibrosis negatively affects bladder function, and there are currently no effective therapeutic interventions to treat bladder fibrosis and restore bladder function. It has been reported that bladder function improves and bladder mass returns to normal after relief of BOO in some, but not all, patients.[32,58]

MicroRNA MicroRNAs are single-stranded, non-coding RNA molecules 19-25 nucleotides in length generated from endogenous hairpin-shaped transcripts.[59] MicroRNAs bind to specific target mRNAs, and either repress translation of mRNA or cause destabilization of mRNA thereby accelerating mRNA degradation.[60] The microRNA-29 (miR-29) family suppresses translation of genes that promote expression of many components of the extracellular matrix, including 20 isoforms of collagen, laminin γ1, fibrillin 1, elastin, and integrin β1.[9, 20-22] Compelling evidence has been reported that miR-29 is decreased in bladders of patients with B006 and in rats with experimentally-created BOO.61, 62 We observed bladder fibrosis and deranged bladder function in mice lacking miR-29a/b1 in the absence of pro-fibrotic stimuli. The strong relationship between miR-29 function and bladder fibrosis makes it a specific and attractive target for modulation and reversal of bladder fibrosis.

The scientific premise of this research is that miR-29 constitutively regulates bladder fibrosis to maintain homeostasis and further that miR-29 has the potential to prevent or reverse bladder fibrosis induced by various urological disorders. The work described in this proposal has the following key translational significance: (1) the research is significant in the context of aging, because bladder extracellular matrix increases—and bladder function deteriorates—with age in humans; 36, 63 (2) the proposed research is applicable to a variety of potential causes of bladder dysfunction, including inflammation that has also been shown to decrease miR-29; 64, 65 and (3) this research has high therapeutic potential, because our preliminary data using a BOO mouse model demonstrate that systemic treatment with miR-29a oligonucleotide mimics suppresses mRNA for key elements of bladder fibrosis. Further, treatment of mice exposed to carbon tetrachloride (CCl4) with intravenous adeno-associated virus (AAV) carrying the miR-29a sequence prevented (AAV-miR-29a given 1 week prior to CCl4 exposure) or reversed (AAV-miR-29a given 4 weeks after CCl4 exposure) hepatic fibrosis triggered by CCl4 treatment.66 The significance of this research is strongly supported by our preliminary findings that lack of miR-29a/b1 creates a profibrotic environment in the bladder wall accompanied by impaired bladder function. These observations support the capacity of miR-29 to function therapeutically to decrease fibrosis in the bladder wall and improve bladder function.

Hypotheses

The hypothesis that lack of miR-29 results in impaired bladder function due to increased extracellular matrix of the bladder wall has not been previously explored. There is scant information regarding the function of miR-29 in the bladder. We will critically test the following hypotheses that: 1. Loss of miR-29a/b1 function causes bladder fibrosis accompanied by impaired bladder function; 2. miR-29a/b1 function in the bladder is crucially dependent upon its tissue-specific expression; and 3. Increased miR-29a/b1 prevents and reverses fibrosis induced by partial bladder outlet obstruction in the mouse.

BACKGROUND

Fibrosis has been described as an imbalance between formation and degradation of extracellular matrix resulting in deterioration of organ function.[67-69] Interestingly, it has been reported that miR-29 reaches its highest levels in mature tissues, presumably in part to maintain homeostasis and prevent fibrosis.70 The transforming growth factor-β (TGF-β) pathway plays a central role in canonical signaling resulting in increased extracellular matrix and fibrosis.69 The relationship between miR-29 and TGF-β is tightly coupled, and each has the capacity to regulate expression of the other. miR-29 also inhibits activity of signaling molecules downstream of activation of TGF-β receptors.

The miRNA-29 (miR-29) family consists of three members (miR-29a, miR-29b and miR-29c) that are encoded by two distinct genomic loci (a/b1 and b2/c) in both human and rodent genomes.74 miR-29a and b1 genes are clustered in the a/b1 locus and share the same promoter, while miR-29b2 and c genes are primed from the b2/c locus by a single promoter.74 miR29-b1 and b2 have identical sequences. All miR-29 have the same seed binding sequence (nucleotides 2-7) and bind to the same set of target genes. The miR-29 family is unique among miRNAs for its capacity to target a cluster of extracellular matrix proteins. Bioinformatic analyses predict conserved binding sites for miR-29 with the genes for 20 collagen isoforms.20 This observation was specific to miR-29, as no other miRNA has been identified with the potential to bind more than 11 of the 20 collagen genes. In addition to suppressing expression of collagens, miR-29 has been shown to decrease abundance of connective tissue growth factor (CTGC), laminin γ1, fibrillin 1, elastin, and integrin β1.9, miR-29a, miR-29b, and miR-29c are all decreased in tissue fibrosis, and systemic administration of synthetic miR-29 prevented or reversed fibrosis in heart, kidney, liver, lung, and skin. miR-29a is more abundant in the mouse bladder than miR-29b and miR-29c combined.

Figure 2B:
FIG. 2B is a microscopic image stained to show miR-29a expression, in which expression is absent in the bladders of KO mice deficient for miR-29a/b1 of the same age. Bar=100 μm.
Figure 2A:
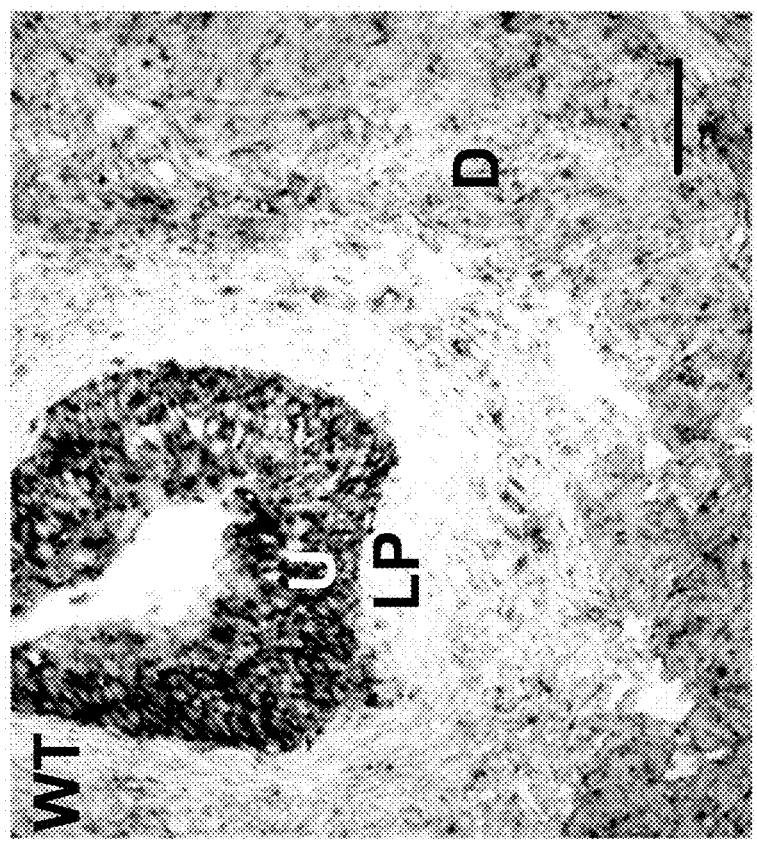
FIG. 2A is a microscopic image stained to show miR-29a expression by the urothelium (U) and detrusor (D), but not the Lamina propria (LP) in 10 week old female wildtype (WT) mice. Bar=100 μm.
Figure 3:
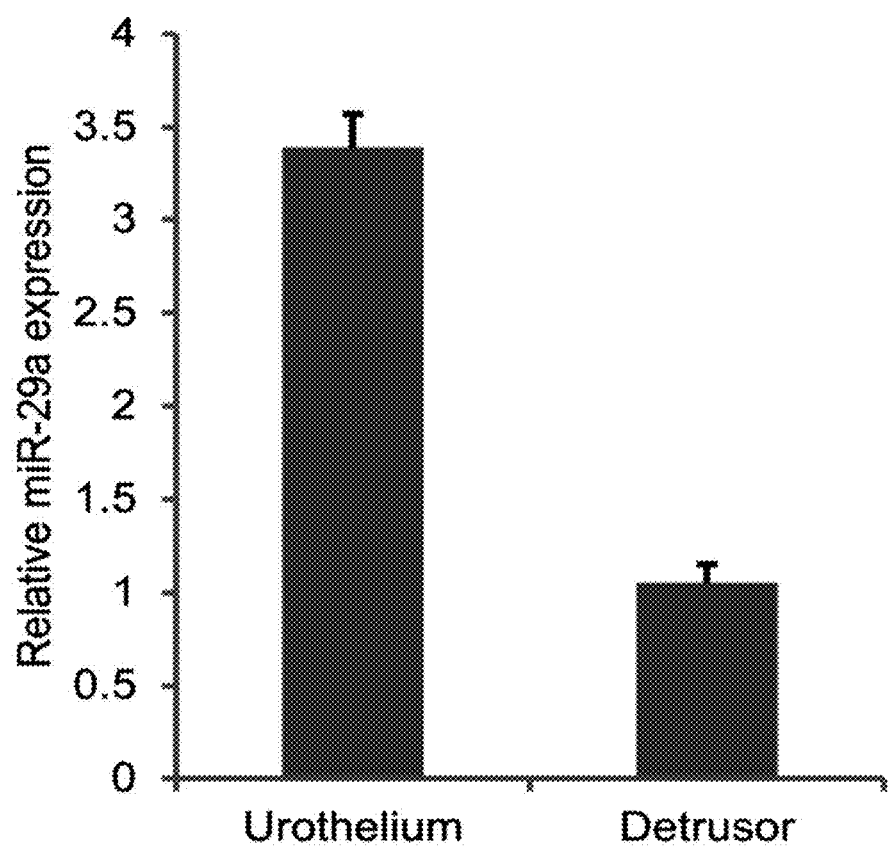
FIG. 3 is a bar graph showing that the abundance of miR-29a was more than 3-fold greater in the urothelium than the detrusor of WT mice as determined by RT-PCR. p<0.01, n=6.

We obtained miR-29a/b1 knock out (KO) mice from Professor Adrian Liston, University of Leuven, Leuven, Belgium.[77] In situ hybridization demonstrated lack of expression of miR-29a in bladders of KO mice (FIG. 2) that was confirmed by RT-PCR. We identified significantly more miR-29a in the urothelium and detrusor by both in situ hybridization using synthetic RNA probes that bind to endogenous miR-29a molecules (Locked Nucleic Acid or LNA Technology™, Exiqon, Woburn, MA) (FIG. 2) and RT-PCR (FIG. 3) in wild-type (WT) mice.

We confirmed the clinical relevance of miR-29a to bladder structure and function by performing in situ hybridization using LNA™ probes specific to human miR-29a using bladder tissue obtained from normal men and men undergoing partial prostatectomy for treatment of BOO due to benign prostatic hyperplasia (BPH). Strong staining for miR-29a was observed in the urothelium and detrusor of all 6 normal controls. Staining for miR-29a was absent (4/6) or weak (2/6) in bladder tissues from 6 BPH patients. The mean age (32 y) of men from whom normal tissue was obtained was significantly lower than that of BPH patients (64 y). Excluding the issue of presence or absence of BOO, these data still indicate a decrease in miR-29a in the bladder as men age and support the translational relevance of the proposed research.

We consistently observed enlarged bladders in miR-29a/b1 KO mice, and a similar observation was made in a very recently described, separately derived line of miR-29a/b1 KO mice.[76] The bladder size of our KO mice (673.4±152.8 mm3, n=8) was significantly greater than WT mice (86.3±15.1 mm3, n=8, p<0.01). We found that urine osmolality was unaffected by lack of miR-29a/b1, and that serum and urine concentrations of glucose were normal. These findings indicate that the enlarged bladder phenotype in KO mice is not due to diabetes insipidus or diabetes mellitus.

Aim 1. Determine Necessity of miR-29 for Normal Bladder Structure and Function

Figure 4B:
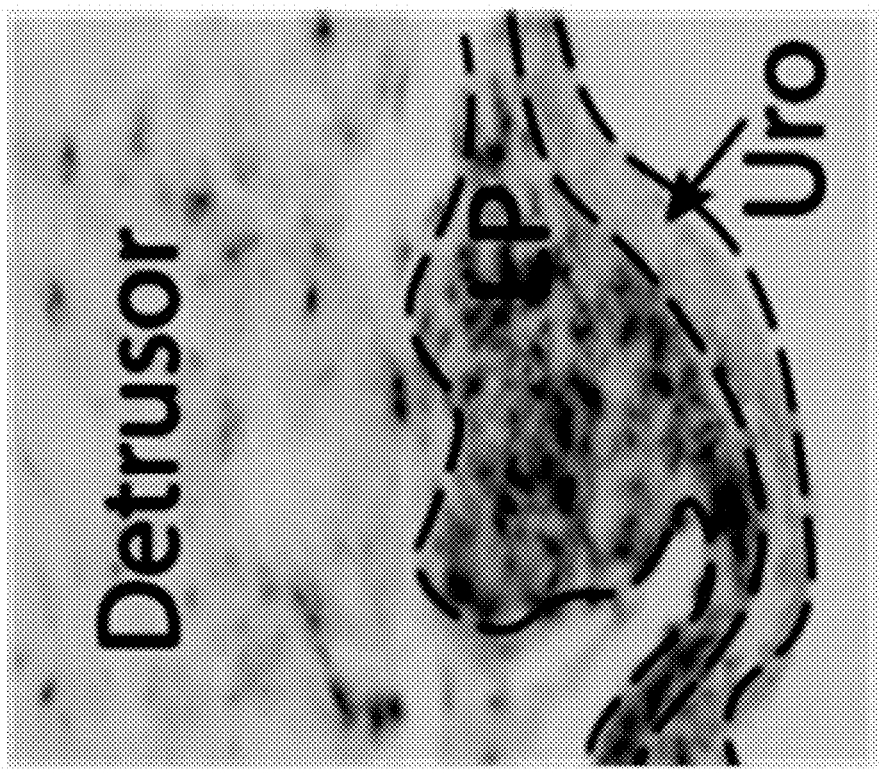
FIG. 4B is an image of in situ hybridization for Col1a1 mRNA in bladders from 10 wk old KO female mice; Col1a1 mRNA was increased in the *Lamina propria* (LP) and detrusor in miR-29a/b1 KO compared to WT of FIG. 4A. Uro—urothelium.
Figure 4A:
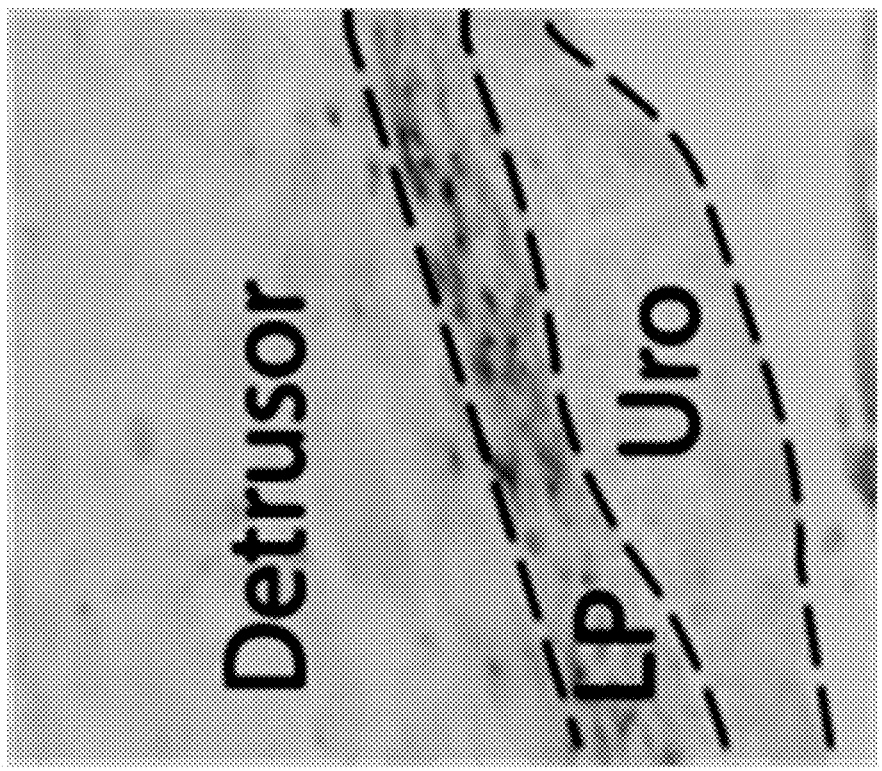
FIG. 4A is an image of in situ hybridization for Col1a1 mRNA in bladders from 10 wk old WT female mice. indicated increased Col1a1 mRNA in the *Lamina propria* (LP) and detrusor in miR-29a/b1 KO compared to W. Uro—urothelium
Figure 5:
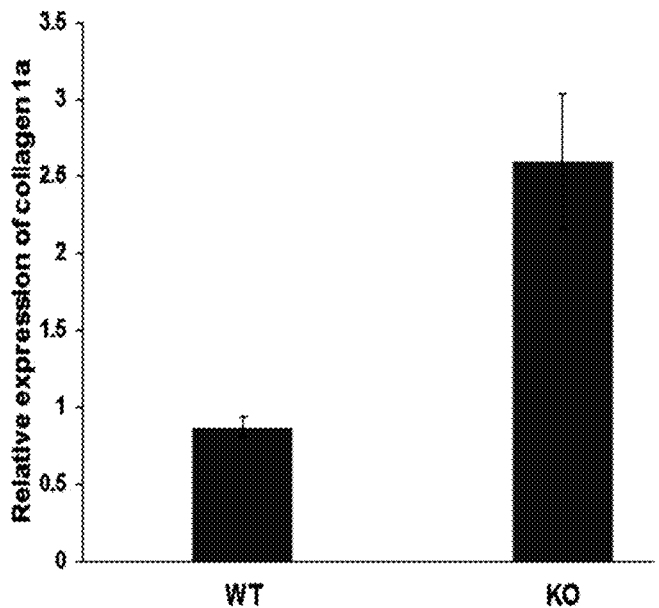
FIG. 5 is a bar graph showing that the abundance of Col1a1 was more abundant in the detrusor of KO 10-week old relative to comparable WT mice as determined by RT-PCR. p<0.01, n=6.
Figure 6:
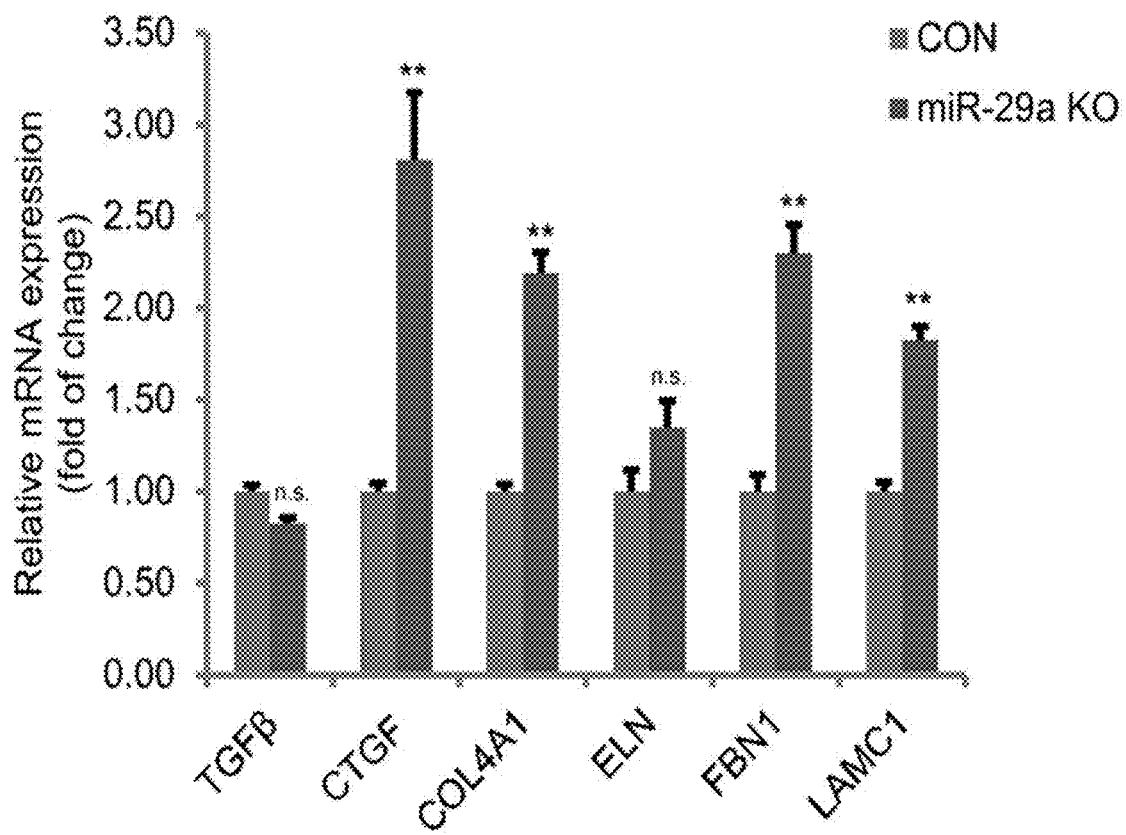
FIG. 6 is a bar graph showing that loss of miR-29a/b1 results in increased message (mRNA) for various components of extracellular matrix.
Figure 7:
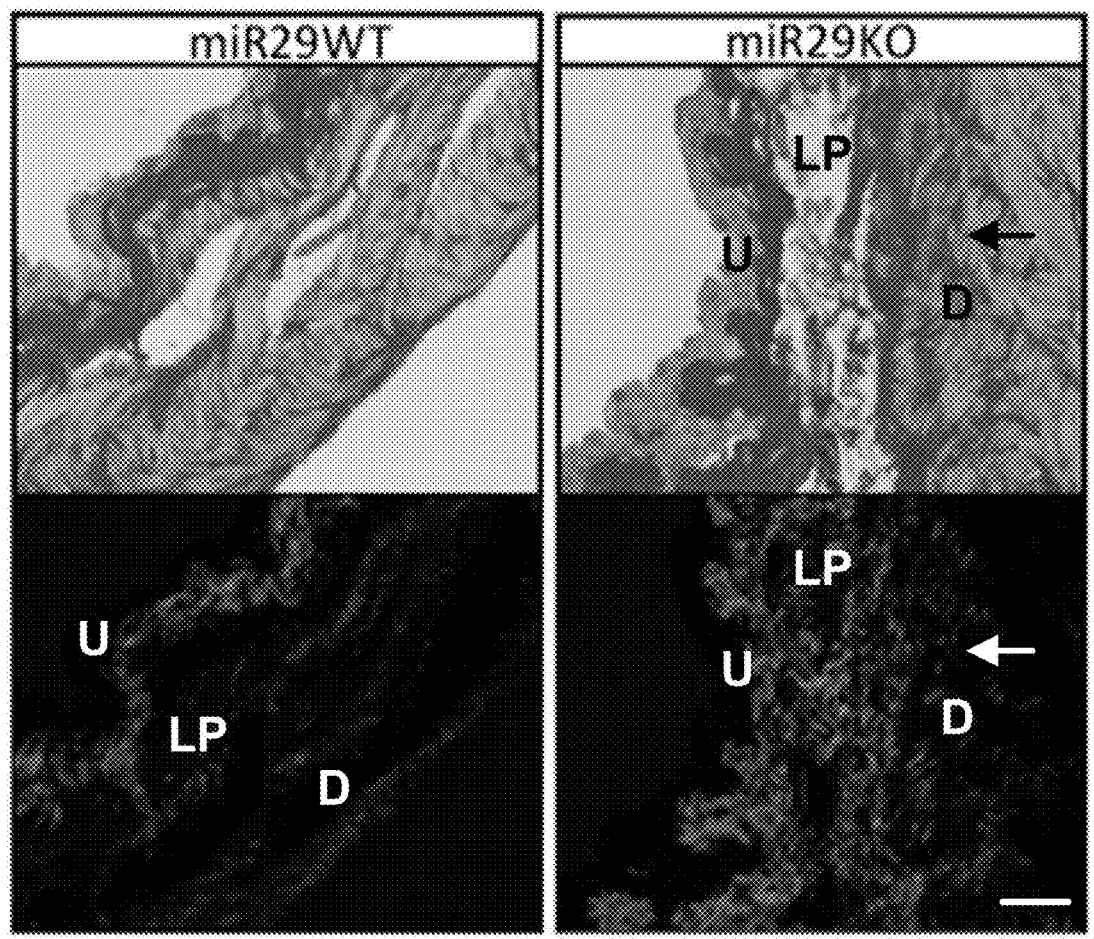
FIG. 7. Fibrillar collagen is increased in the *Lamina propria* and detrusor of bladders from miR-29a/b1 KO mice. Sections of bladders from 3 month old male miR-29a/b1 KO mice and WT male mice were stained with picrosirius red (PSR) and viewed with light microscopy (upper panels) and polarized light (lower panels). PSR-collagen binding birefringes when viewed with polarized light, confirming the presence of fibrillary collagen (same sections in upper and lower panels). Arrows indicate fibrillar collagen in detrusor of KO bladders compared to lack of fibrillar collagen in detrusor of WT bladders. Bar=100 µm.
Figure 8A:
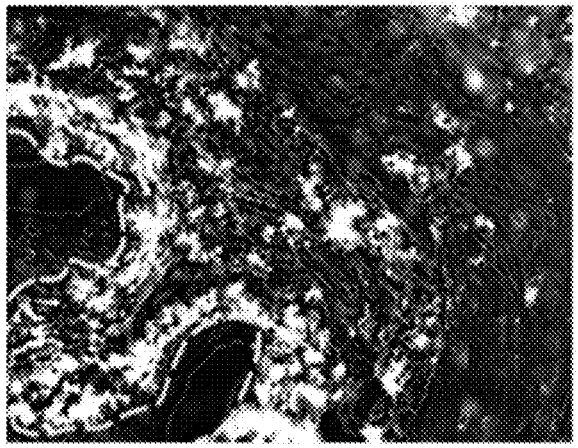
FIG. 8A shows RNAscope labeling of Col1a1 mRNA viewed in brightfield for a section of WT bladder. Col1a1 is imaged in white.
Figure 8B:
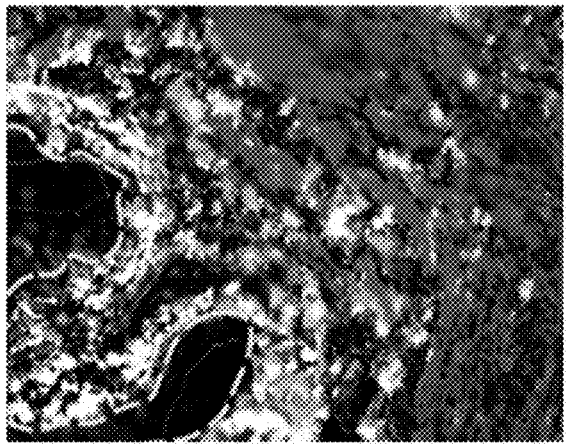
FIG. 8B shows RNAscope labeling of Col1a1 mRNA viewed with multiplex IHC for the same WT bladder section of FIG. 8A. Col1a1 is imaged in white. Vimentin identifies fibroblasts, smooth muscle actin identifies detrusor, and nuclei are stained with DAPI. The dotted line indicates the separation between the urothelium and *Lamina propria*. Co-localization of Col1a1 mRNA and fibroblasts is indicated. An overlap of nuclei and smooth muscle actin is also indicated.
Figure 8C:
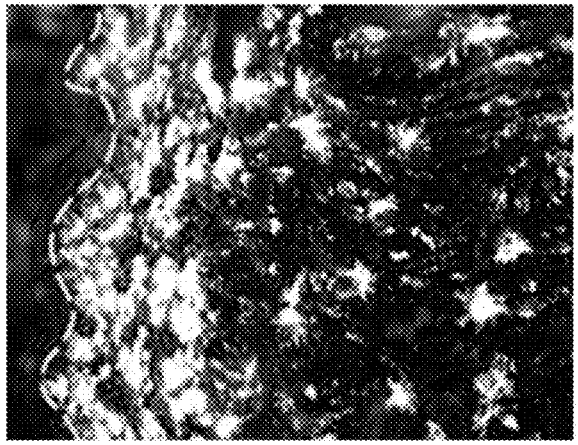
FIG. 8C shows RNAscope labeling of Col1a1 mRNA viewed in brightfield for a section of KO bladder. Col1a1 is imaged in white.
Figure 8D:
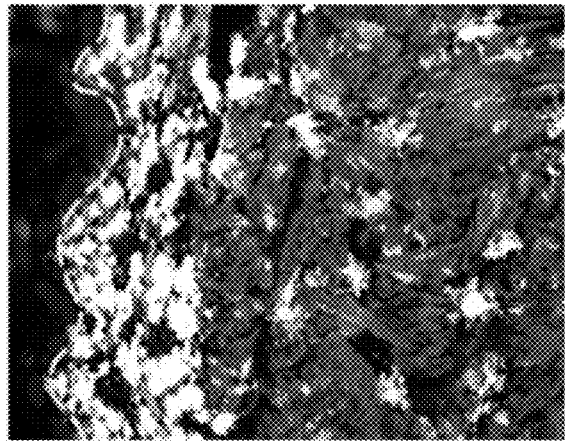
FIG. 8D shows RNAscope labeling of Col1a1 mRNA viewed with multiplex IHC for the same KO bladder section of FIG. 8C. Col1a1 is imaged in white. Vimentin identifies fibroblasts, smooth muscle actin (red) identifies detrusor, and nuclei are stained with DAPI. The dotted line indicates the separation between the urothelium and *Lamina propria*. Co-localization of Col1a1 mRNA and fibroblasts is indicated. An overlap of nuclei and smooth muscle actin is also indicated.

Rationale Fibrosis has been described as an imbalance between formation of extracellular matrix and degradation resulting in deterioration of organ function.[67-69] Our preliminary data strongly indicate that loss of miR-29a/b1 results in increased message (mRNA) for Col1a1 (FIGS. 4 and 5) and other components of extracellular matrix (FIG. 6). Fibrillar collagen is increased in the *Lamina propria* and detrusor of KO mice (FIG. 7), further supporting the premise of this research. It is assumed that fibrillar collagen is produced primarily by fibroblasts and myofibroblasts in vivo. Studies performed in support of Sub-Aim 1.1 will identify the location of mRNA for components of extracellular matrix and further will determine cell types that express this mRNA. Data accompanying Sub-Aim 1.2 illustrate the derangement of bladder function in these mice. To ensure rigor and reproducibility, we will test both males and females over a range of ages to assess the effects of gender and aging. The goals of this aim are to: 1. Determine the effects of global loss of miR-29a/b1 on bladder histology and local expression of relevant mRNA in male and female WT and KO mice at different ages (2, 4, and 6 months); 2. Characterize in vivo bladder function of mice of both sexes at these ages; and 3. Determine in vitro contractility of bladder tissue from mice of both sexes at these ages in response to electrical field stimulation, muscarinic agonists, and purinergic signaling. The scientific rigor of the studies to be performed is also supported by the use of multiple techniques to confirm findings (e.g., in situ hybridization and RT-PCR; immunoblotting and IHC).

Sub-Aim 1.1 Determine the Effects of Global Loss of miR-29a/b1 on Bladder Histology and Local Expression of Relevant mRNA Approach These experiments will be performed to characterize the effects of loss of miR-29a/b1 on the extracellular matrix of the bladder wall. Composition of the bladder wall will be assessed by histology, immunohistochemistry, and immunoblotting. mRNA expression in the urothelium and detrusor will be determined by in situ hybridization (ISH), and cells producing specific mRNA will be identified by combining ISH with multiplex immunohistochemistry (IHC) using techniques developed by our co-Investigator Dr. Chad Vezina.[78] RNA sequencing (RNA-seq) of heart tissue from miR-29a/b1 KO mice indicated the presence of tissue-specific changes in RNA expression in KO compared to WT mice that identified specific changes relating to altered structure and function. RNA-seq will be performed to identify additional targets that may contribute to altered bladder structure or function in the absence of miR-29a/b1.

Histological detection of fibrotic tissue in bladder wall Bladder tissues will be fixed in 4% paraformaldehyde and embedded in either paraffin or OCT. Tissue imbedded in OCT will be frozen at −80° C. until used for cryosectioning. Histological evaluation will be performed by light microscopy after staining with hematoxylin and eosin (H&E). Tissues will be stained with picrosirius red (FIG. 7) and viewed with polarized and fluorescent microscopy to determine abundance of fibrous tissue. In addition, these tissues will be viewed with second harmonic generation imaging (SHG). Fluorescent and SHG images will be processed as described previously using CT-FIRE software, a program developed by The Laboratory for Computational Imaging at the University of Wisconsin that allows objective measure and molecular analysis of collagen alignment, fiber length, quantity, density, and size in situ with high throughput.[79,80] This approach will allow us to critically evaluate changes in the extracellular matrix in the presence or absence of miR-29a.

Immunohistochemistry (IHC) and immunoblotting IHC will initially be performed using primary antibodies to detect and localize Col1a1, Col4a2, laminin, fibronectin, connective tissue growth factor, and elastin. Protein will be isolated from whole bladders or from the urothelium/submucosa and detrusor separately for performance of immunoblotting for these proteins to confirm IHC results. IHC performed for detection of components of the TGFβ signaling pathway is inconsistent. Immunoblotting will be performed to confirm these results. Protein will be extracted from urothelium/submucosa and detrusor from mice at 2, 4, and 6 months of age, and immunoblotting will be performed to assess relative abundance of TGFβ, connective tissue growth factor (CTFG), SMAD3, P-SMAD3, ERK, and P-ERK (ERK mediates non-canonical fibrotic pathway initiated by TGFβ). Validated identification of fibroblasts by immunohistochemistry is extremely challenging and requires use of multiple antibodies.[78] In conjunction with our co-Investigator, Dr. Chad Vezina, we have developed a technique for multiplex immunohistochemistry to identify fibroblasts and myofibroblasts in situ by sequentially exposing tissue sections to antibodies to vimentin, fibroblast specific protein 1, and α-smooth muscle actin. Fibroblasts stain positive for vimentin and fibroblast-specific protein 1, and myofibroblasts stain positive for these, as well as α-smooth muscle actin.[78]

In situ hybridization (ISH) FIG. 8 demonstrates the feasibility and utility of combining ISH and multiplex IHC to identify the location and type of key cells that participate in processes that result in increased extracellular matrix within the bladder wall. Thus, these studies strongly support the scientific premise of the research. ISH will be performed to confirm the presence and location of miR-29a and mRNA for proteins of interest. Locked RNA™ probes for miR-29a will be obtained from Exiqon, Woburn, MA. RNAscope® technology (ACD, Newark, CA)[81] provides greater fidelity in identifying specific cells expressing the mRNA of interest than does standard ISH, and we will therefore perform ISH using RNAscope® in conjunction with multiplex IHC (FIG. 8). Note that Col1a1 mRNA was particularly abundant in the *Lamina propria* in both FIGS. 4 and 8, and that Col1a1 was specifically associated with fibroblasts in the detrusor (FIG. 8). Similar studies will be performed with RNAscope® probes targeting connective tissue growth factor (CTGF), fibronectin, and laminin. Combining ISH with multiplex IHC will allow us to critically identify the cellular location of specific mRNAs of interest. Tissues can also be stained for evidence of cellular division using antibody to Ki-67 to determine whether alterations in abundance of cells is the result of cellular migration or proliferation.

RNA Sequencing (RNA-Seq) will be performed to clarify the relative roles of urothelium and detrusor in signaling via miR-29a/b1. mir-29a is clearly more abundant in the urothelium than in the detrusor. However, both message for Col1a1 and the protein are abundant in the *Lamina propria* (WT and KO) and detrusor of KO mice but absent from the urothelium of all strains of mice. These studies will be performed to determine whether patterns of mRNA expression in the urothelium of miR-29a/b1 KO and WT are similar while those in the detrusor vary, with greater expression of mRNA associated with extracellular matrix present in detrusor of KO mice. Differential expression of mRNA in either the urothelium or detrusor of WT compared to KO mice would suggest new pathways of signaling resulting in abnormal bladder structure and function. These findings would be confirmed by RT-PCR and evaluated for further testing to determine fundamental mechanisms of regulation of bladder structure and function by miR-29a/b1.

Cell Isolation Bladder tissue will be collected from WT and KO mice, and the urothelium/*Lamina propria* will be gently dissected from the detrusor/serosa.82 Single cell suspensions will be prepared for isolation of urothelial or detrusor cells by fluorescence-activated cell sorting (FACS). Flow Cytometry will isolate urothelial cells using a primary cytokeratin 7 antibody (ab9021, abcam, Cambridge, MA)83 and detrusor cells using a primary smooth muscle myosin, heavy chain (SMMHC; ab212660, abcam, Cambridge, MA) antibody.[84]

Construction of RNA and small RNA-seq libraries Total RNA will be isolated from urothelial or detrusor cells obtained from WT or miR-29a/b1 KO mice. RNA-seq studies will be performed by the University of Wisconsin Biotechnology Center. Total RNA is submitted and verified for purity and integrity via the NanoDrop2000 Spectrophotometer and Agilent 2100 BioAnalyzer, respectively. Samples that meet the Illumina sample input guidelines are then prepared according the TruSeq® Small RNA Sample Preparation Guide. For each TruSeq Small RNA library preparation, 3' and 5' RNA Adapters are sequentially ligated to the 3'-hydroxyl and 5'-phosphate groups on microRNA molecules included in the 1 ug total RNA input (RNA isolation method retains small RNA molecules) according to the Illumina's TruSeq Small RNA Sample Preparation Guide (RevD). 5' and 3' Adapter-ligated RNA is reverse transcribed with SuperScript II Reverse Transcriptase (Invitrogen, Carlsbad, California, USA) and random primers to create cDNA constructs. cDNA constructs that have the adapter molecules on each end are selectively enriched by PCR using Phusion™ DNA Polymerase and Illumina's genomic DNA primer set. Amplified cDNA constructs are gel purified on 6% PAGE gels (Invitrogen, Carlsbad, California, USA), excising 145-160 bp bands from Ethidium Bromide stained gels. Size selected cDNA constructs are purified from gel fragments using a gel breaker tube and concentrated by ethanol precipitation. Quality and quantity of the DNA is assessed using an Agilent DNA HS series chip assay and Invitrogen's PicoGreen detection dye. Cluster generation and sequencing are performed on the Illumina cBot and HiSeq2500 following manufacturer's instructions. RNA-seq will be performed using RNA extracted from urothelium or detrusor from male and female WT and KO mice at 3, 6, and 9 months of age (4 mice of each genotype at a given age; WT compared to KO). This will result in 12 RNA-Seq runs (2 genders×3 ages for urothelium and detrusor).

Quantitative RT-PCR Total RNA will be isolated from the urothelium and detrusor for performance of quantitative RT-PCR. RT-PCR will be performed to confirm abundance of mRNA for targets of particular interest detected by immunohistochemistry and RNA-seq.

Results and Alternative Approaches

The goal of these experiments is to analyze the effects of miR-29a/b1 on dysregulation of pathways that control formation of extracellular matrix and fibrous tissue within the tissues that comprise the bladder wall. We have limited our use of RNAscope® in preliminary studies to cellular localization of mRNA for Col1a1 due to expense and time required for these studies. We can readily expand application of this technique in conjunction with multiplex IHC to localize other mRNAs of interest to specific cell types. RNA-seq data will be scrutinized for information on relative abundance of message for substances that modulate fibrous tissue after formation. In addition to playing a significant role in inhibiting synthesis of components of fibrosis and extracellular matrix, miR-29 has been reported to regulate enzymes responsible for mediating cross-linking of collagen such as lysyl oxidase and lysyl oxidase-like 2, 12, 85, 86 as well as matrix metalloproteinases, including MMP2, MMP14, and MMP15, that degrade extracellular matrix proteins.12, 87-89 Inhibition of collagen crosslinking and the relative availability of enzymes that act to break down extracellular matrix may be vital components of mechanisms by which miR-29 suppresses formation of extracellular matrix and exerts a therapeutic effect on established fibrosis. Depending upon results obtained, these could be useful pathways to consider for further modulation of bladder fibrosis. In addition to confirming alterations in message for pathways associated with fibrosis, results of RNA-seq analysis of myocardium from miR-29a/b1 KO mice identified key metabolic targets for further study.76 It is entirely possible that alterations in metabolism of detrusor regulated by miR-29a/b1 may contribute to impaired bladder function.

An alternative approach would be studies with isolated urothelial or detrusor cells. Urothelial and detrusor cells both express TGFβ receptors and respond to treatment with TGFβ.90, 91 We have extensive experience with isolation and culture of urothelial cells92-95 and can successfully isolate primary detrusor cells. Primary cultures of urothelial and detrusor cells from various genotypes of mice could be used, as well as primary human urothelial and detrusor cells obtained from ScienCell Research Laboratories (Carlsbad, CA). Cells would be cultured from WT and KO mice, and miR-29a/b1 could be deleted or restored by transfection with either small interfering-miRNA (simiRNA) or miR-29a/b1 oligonucleotides.

Sub-Aim 1.2 Determine the Effects of Global Loss of miR-29a/b1 on In Vivo Bladder Function Approach These experiments will be performed to characterize the effects of loss of miR-29a/b1 on in vivo function of the bladder. We have generated new software that improves consistency and reproducibility of result of void spot assay testing.[96,97] We will also use a custom-designed system for perform uroflowmetry, including use of software we have developed for data collection in this system. In vivo bladder function will be evaluated in male and female mice (WT and miR-29a/b1 KO) at 2, 4, and 6 months of age. Our experience with these techniques and development of new software provide confidence regarding reproducibility and reliability of results.[96-98]

Void Spot Assay (VSA) VSA will be performed as previously described.[96,98] Individual mice will be placed in standard polycarbonate mouse cages once daily for 3 days prior to testing to acclimate them to testing conditions. Mice will have free access to water prior to testing. Mice will be placed in standard cages in with 16×26 cm filter papers taped to the bottom of the cage for 4 hours between 9 AM and 2 PM. Filter papers will be collected for imaging under incident ultraviolet light (AutoChemi UVP Bioimaging System, Upland, CA) to reveal urine spots. Number, distribution, and size of urine spots will be analyzed using a software plugin for ImageJ (NIH) that we recently described.[97]

Uroflowmetry will be performed as previously described.[99] Mice will be acclimated to Nalgene metabolic cages (Bellmore, NY) positioned over balances (Mettler Toledo, Columbus, OH) and then tested for 24 hours. Each metabolic cage has an individual Raspberry Pi computer and camera (Raspberry Pi Foundation, San Jose, CA), and data are stored on a desktop PC. Frequency and volume of urinary voids are determined, and video recordings are analyzed to characterize voiding events as straining, dribbling, or normal stream.

Figure 9A:
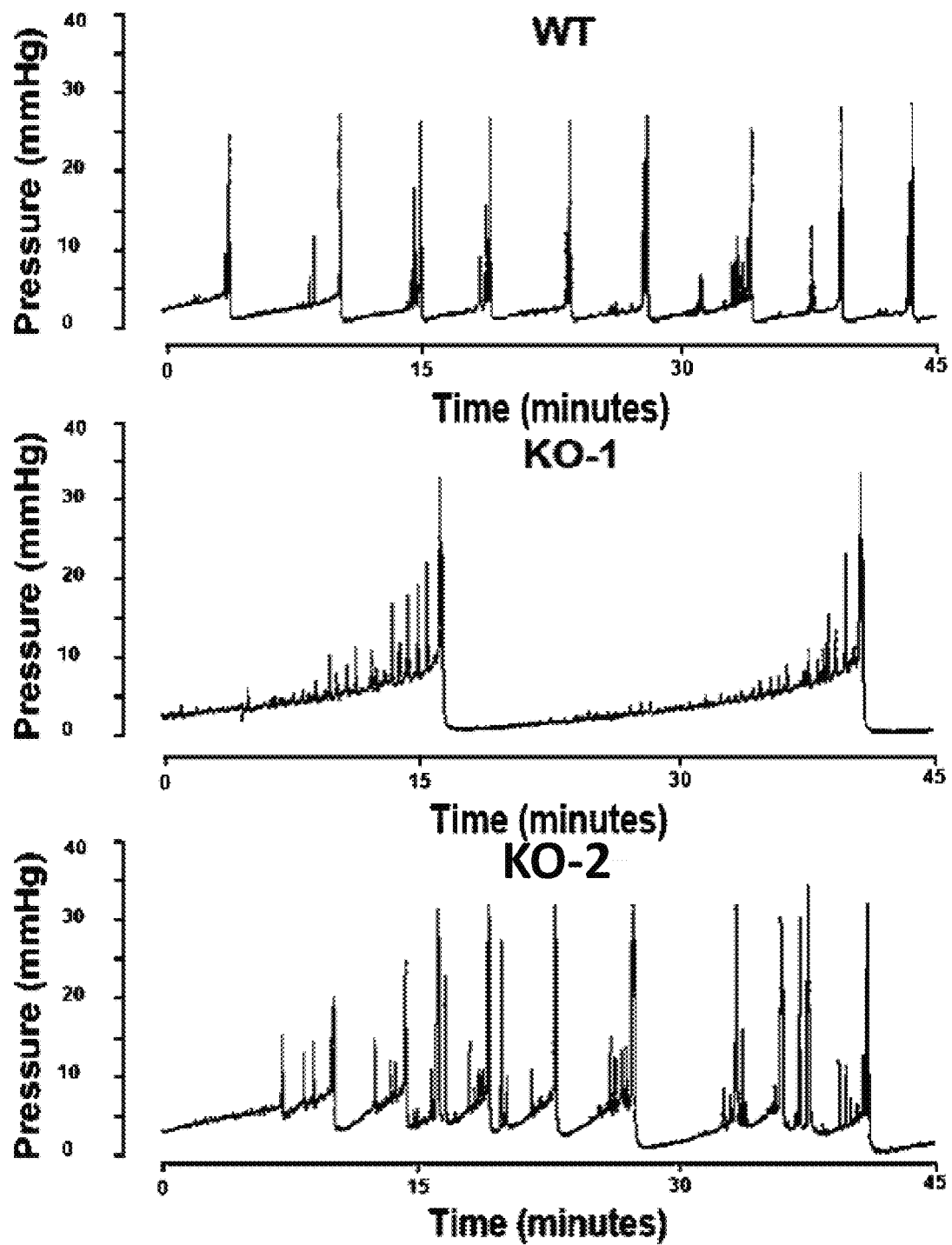
FIG. 9A contains representative CMG tracings of 10 week old female WT and miR-29a/b1 KO mice showing that all WT mice had a normal voiding pattern. Two distinct patterns of micturition occurred in KO mice. One pattern was characterized by prolonged interval time between micturitions (intercontractile interval or ICI) and a series of non-voiding contractions prior to micturition (KO-1). The other pattern was characterized by a series of contractions with release of droplets of urine between coordinated micturitions (KO-2).
Figure 9B:
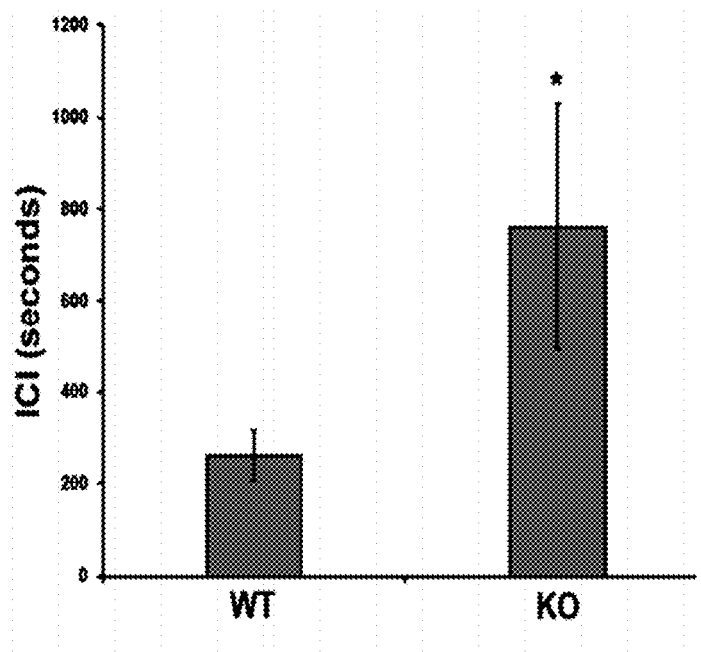
FIG. 9B is a bar graph showing that ICI was significantly increased in KO mice. n=6-8. *p<0.05.
Figure 9C:
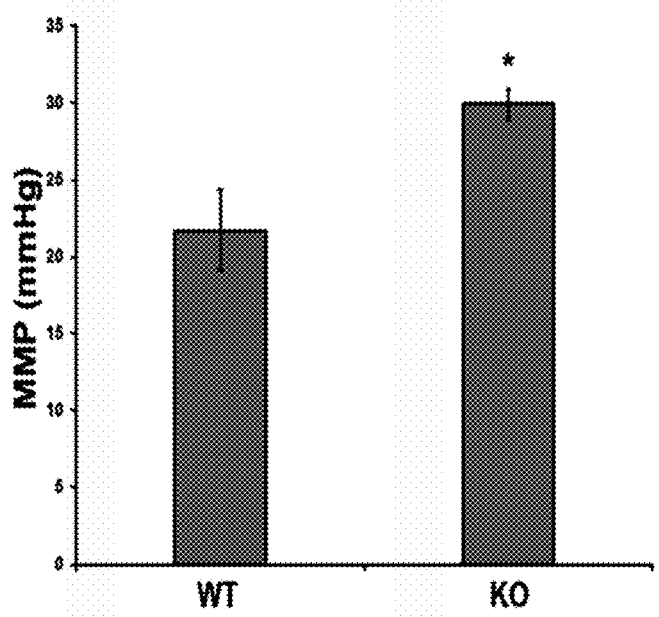
FIG. 9C is a bar graph showing that maximal micturition pressure (MMP) was higher in KO mice than in WT mice. n=6-8. *p<0.05.
Figure 10A:
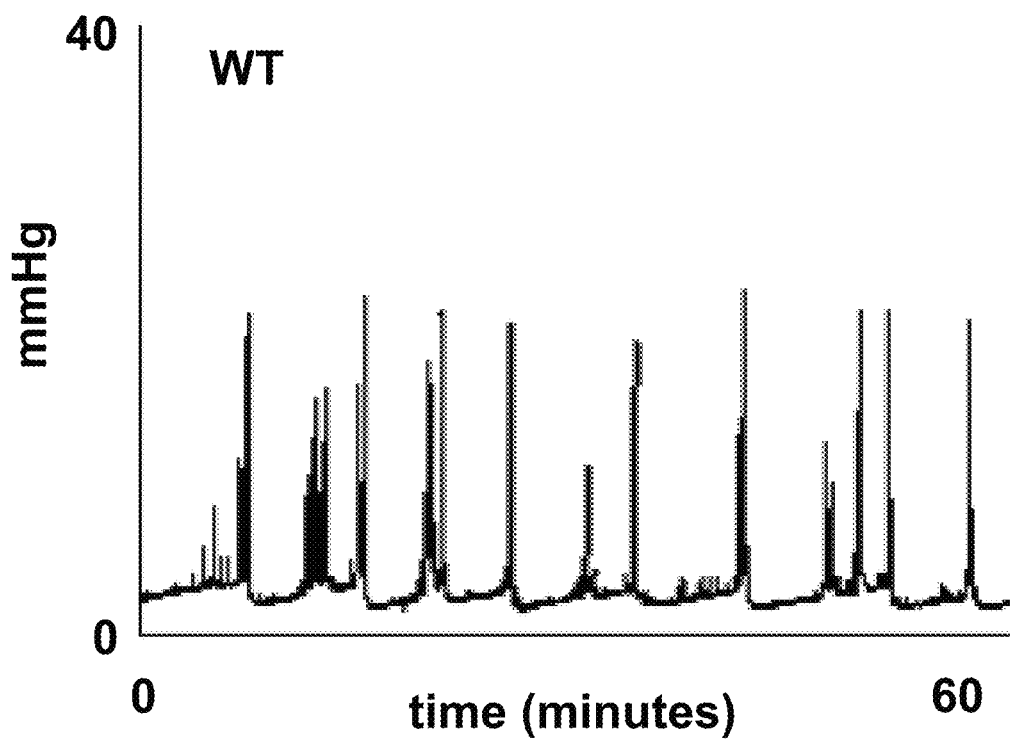
FIG. 10A is a cystometrogram recordings from a 16 week old male WT mouse using an infusion rate of 0.8 ml/hr. The CMG tracing from the WT mouse was obtained over 60 minutes and includes 9 voiding contractions. The pressure scale on the Y axis is from 0 mm Hg (bottom of chart for WT) to 40 mm Hg (top of grid). The observed patterns were consistent for 4 WT mice.
Figure 10B:
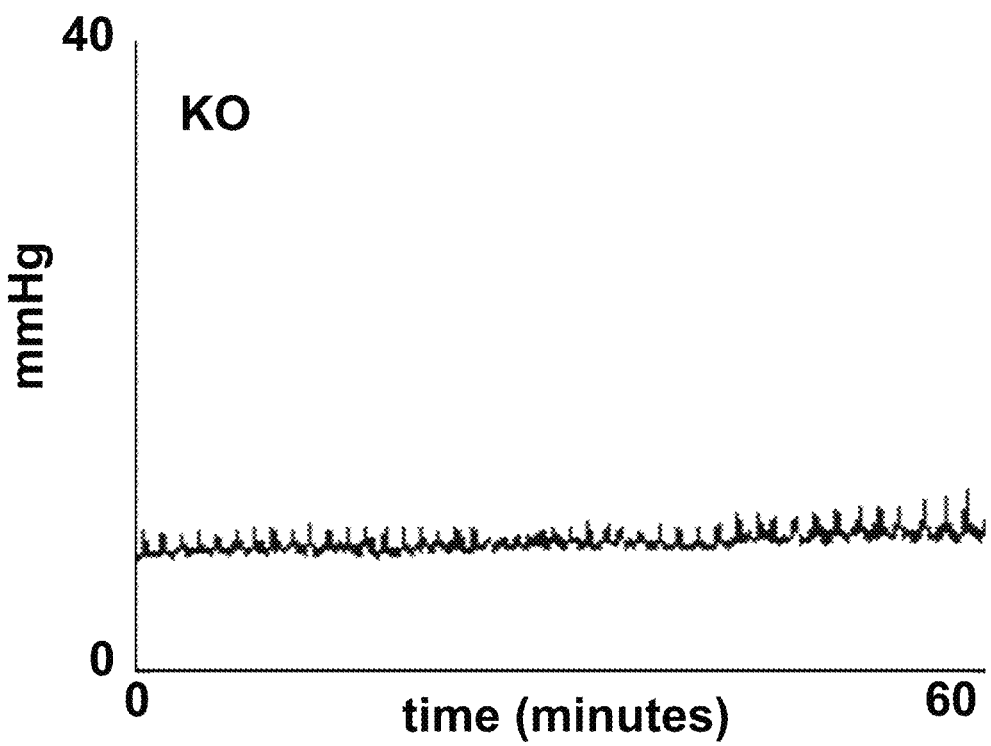
FIG. 10B is a cystometrogram recordings from a 16 week old male miR-29a/b KO mouse using an infusion rate of 0.8 ml/hr. The CMG tracing from the KO mouse was obtained over 60 minutes, the mouse generated a void that was characterized by intermittent discharge of urine (dribbling) rather than a consistent stream. The pressure scale on the Y axis is from 0 mm Hg (first visible mark for KO) to 40 mm Hg (top of grid). The observed patterns were consistent for KO mice.
Figure 11A:
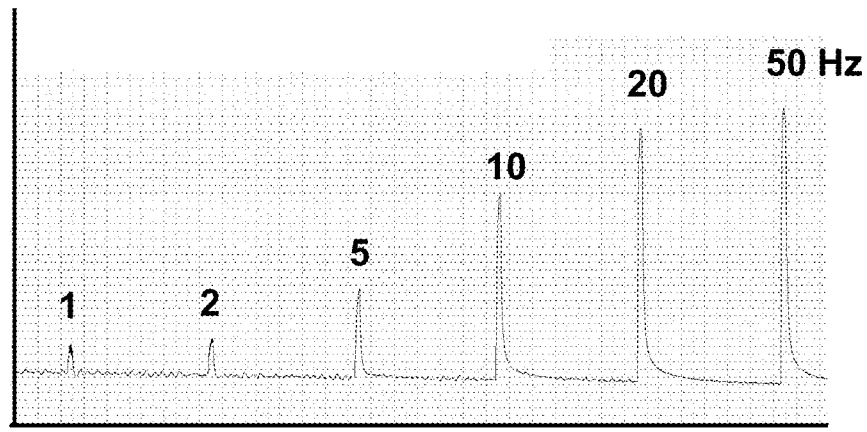
FIG. 11A is a graph showing the response of isolated WT bladder tissue to electrical field stimulation in the absence (A) of atropine (1 µM).
Figure 11B:
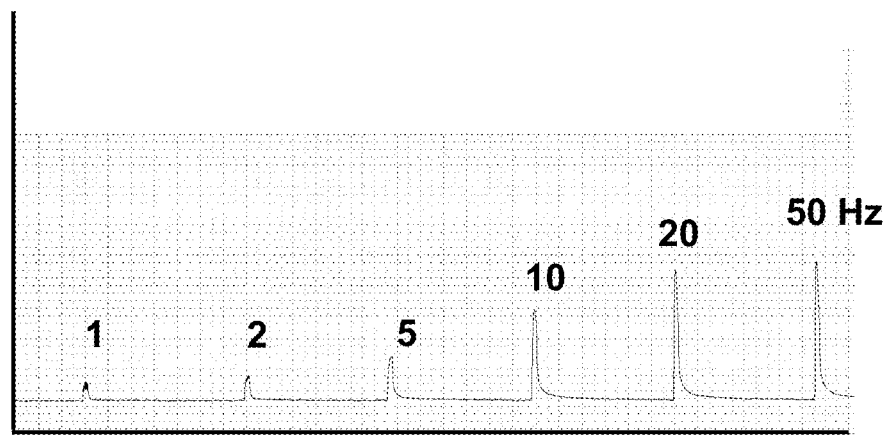
FIG. 11B is a graph showing the response of isolated WT bladder tissue to electrical field stimulation in the presence of atropine (1 µM).
Figure 11C:
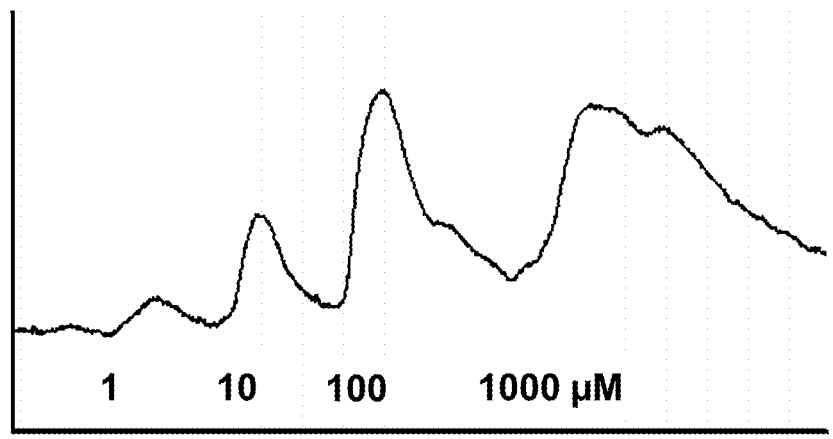
FIG. 11C is a graph showing the concentration-response curve to increasing concentrations of ATP.

Cystometry Cystometry will be performed as previously described.[98,100] Mice will be anesthetized with urethane (1.43 g/kg, subcutaneous injection), and a PE 50 cannula will be inserted into the bladder via an abdominal incision. The cannula will be connected to a physiological pressure transducer (Memscap A S, Norway) and infusion pump (Harvard Apparatus, Holliston, MA). Room temperature saline will be infused (0.8 mL/hour) for 60-90 minutes to elicit repetitive micturition cycles. Voided volume will be weighed using Grass FT03 force transducers. Data will be recorded continuously using a PowerLab data collection system (ADInstruments, Colorado Springs, CO) connected to a PC computer. At least 4-6 reproducible micturition cycles will be recorded and analyzed to determine intercontractile interval (ICI; time between micturition events), maximal voiding pressure, micturition threshold (pressure at which voiding begins), functional bladder capacity (defined as the saline infusion rate multiplied by the ICI), void volume, non-voiding bladder contractions (intravesical pressure increases >5 mm Hg during the filling phase without release of fluid from the urethra). Bladder capacity, residual volume, and voiding efficiency will be determined by stopping the infusion of saline, emptying the bladder via the catheter, and then infusing saline to stimulate a void. Bladder capacity will be considered the volume required to stimulate a void, and residual volume will be the amount of fluid emptied from the bladder via the catheter at the conclusion of voiding. Voiding efficiency will be calculated using the following formula: bladder capacity-residual volume/bladder capacity×100. FIG. 9 shows representative cystometrogram (CMG) tracings of female WT and KO mice (A). All female WT mice had normal voiding patterns. The intercontractile interval (ICI, time between voids) was significantly increased in KO mice, confirming that KO mice had a larger functional bladder capacity (B, p<0.05), and the maximal voiding pressure was greater in KO than WT mice (C, p<0.05). Cystometry also revealed two distinct patterns of micturition in KO mice. One pattern was characterized by prolonged ICI and a series of non-voiding contractions (increased intravesicular pressure in the absence of voiding) prior to micturition (FIG. 9A, KO-1). The other pattern of voiding by KO mice was characterized by irregular frequency of voids preceded by non-voiding contractions with release of droplets of urine between coordinated voids (FIG. 9A, KO-2). These events were not considered to be complete voidings, because of the small volume of urine released and the observation that bladder pressures did not return to baseline after contractions and release of urine droplets. FIG. 9B provides the summation of all recordings for female KO mice. The observed changes of bladder function in these mice (increased bladder volume, increased maximal voiding pressure, increased intercontractile interval, and increased non-voiding contractions) are consistent with those expected during the early phases of increased extracellular matrix. The structural changes present appear to have contributed to urine retention and increased pressure required to expel urine. We anticipate that as the structural changes become more severe, the voiding phenotype will show further derangement. In this context, the data presented in FIG. 10 (CMG tracings from 4 month old male WT and KO mice) are of particular interest. Four mice of each genotype were tested, and consistent recordings were obtained from all. These data strongly suggest that the function of bladders in 16 week old male mice may be more severely affected by lack of miR-29a/b1 than those of 10 week old female KO mice. We have not had sufficient mice to compare bladder fibrosis in males and females of similar ages, and this will be performed in the proposed experiments.

Results and Alternative Approaches

We anticipate that bladder function will deteriorate as mice age and that this will progress more rapidly in males than female. We will compare the results of in vivo testing with results of in vitro testing (Sub-Aim 1.2), as well as histological evaluation of bladder tissues of mice as they age (Sub-Aim 1.3) to compare accumulation of fibrous tissue and extracellular matrix in the bladder wall with bladder function. We anticipate that the detrusor will initially hypertrophy and bladder compliance will increase. As mice age and fibrous tissue in the bladder wall increases, we expect to see weaker contractions, incomplete bladder emptying, decreased bladder compliance, and that at least some mice will exhibit loss of coordinated bladder contraction with urine voids consisting of expulsion of a few droplets or dribbling of urine. If we observe bladder dysfunction in the absence of structural changes in the bladder wall, we will consider 3 primary alternatives: 1. Loss of miR-29a/b1 induces urethral obstruction due to fibrosis of the urethra or peri-urethral tissues; 2. Loss of miR-29a/b1 affects bladder permeability; or 3. Loss of miR-29a/b1 affects innervation. Should further studies become necessary, we can assess the first alternative by examining the urethra in female, and the prostate and prostatic urethra in male, WT and KO mice for histological evidence of fibrosis. We will also use a technique for assessing urine flow by injecting microbubbles into the bladder of a mouse while imaging the mouse with micro-ultrasonography. This technique was developed to measure blood flow in mice, and we have adapted it to study urine flow. If bladder permeability is increased by loss of miR-29a/b1, we should see evidence of inflammation (bladder wall edema, leukocytic infiltration). Should we need to assess permeability of the bladder wall, we have the capability to do this in vivo by intravesical instillation of tracers and in vitro by testing bladder tissue permeability in Ussing chambers.101,102 We have experience in evaluating bladder nerve function in vitro by patch-clamp,103 and we can inject tracer dyes into the bladder wall to identify bladder-specific neurons, if required.

Sub-Aim 1.3 Determine the Effects of Global Loss of Mir-29A/B1 on In Vitro Bladder Contractility Approach In vitro contractile capacity of the detrusor will be evaluated in male and female mice (WT and miR-29a/b1 KO) at 3, 6, and 9 months of age by isolated muscle bath studies.

Isolated muscle bath studies Contractile function of the bladder wall will be evaluated in the presence and absence of urothelium as previously described.99, 104-106 Mice will be euthanized, and bladders rapidly collected. Bladders will be placed in oxygenated (95% O2/5% CO2) modified Krebs solution (pH 7.4; NaCl, 119; NaH2PO4, 1; KCl 4.7; CaCl2, 2.5; MgCl2, 0.5; NaHCO3, 7; and glucose, 25; all concentrations in mM) maintained at 37° C. Bladders will be cut into longitudinal strips and either left intact or denuded of the urothelium by careful dissection with scissors. Tissue strips will be weighed and suspended in 10 ml tissue baths containing oxygenated modified Krebs solution maintained at 37° C. Tissues will be secured to the bath and to force displacement transducers (Grass FT-03, Grass Instruments). One gram of tension will be applied, and tissues will be allowed to equilibrate for 1 hour. Concentration-response curves will be generated in response to increasing concentrations of carbachol (0.01 to 100 µM). Response to electrical field stimulation (EFS, simulating nerve stimulation) will be determined by placing the tissues between platinum-coated electrodes and applying a current of 12 V and 1 ms pulse at an increasing frequency of 1-50 Hz using a Grass S88 stimulator (Astro-Med Industrial Park, West Warwick, RI). The purinergic component of EFS-induced contraction will be evaluated in the presence of 1 µM atropine to block cholinergic effects. Cholinergic responses will be evaluated by treatment of bladder strips with 10 µM α,β-methylene ATP to desensitize P2X receptors prior to EFS. Additionally, cumulative concentration response curves in response to increasing concentrations of ATP (1-1000 µM) will be evaluated in bladder strips not previously exposed to α,β-methylene ATP.99 All tissues will be exposed to KCl (120 mM) at the end of experiments to confirm viability and response. Response curves will be analyzed to determine that frequency or concentration resulting in 50% maximal response. The weight and length of tissue preparations will be measured and data will be normalized to cross section area. Cross-sectional area will be determined using the following formula: mass/length×density (with the assumed density of bladder tissue=1.05).107

Results and Alternative Approaches

We anticipate that strength of detrusor contraction in response to electrical field stimulation, carbachol, or activation of purinergic receptors in miR-29a/b1 KO compared to WT bladder will decline as mice age. We further expect that detrusor contractility will be lost more rapidly in male than female KO mice. Electrical field stimulation induces contraction due to stimulation of innervation of the detrusor. Exposure to carbachol stimulates muscarinic receptors within the detrusor, while atropine-resistant bladder contraction appears to be the result of purinergic signaling.106,108 If the response to electrical field stimulation in bladder tissue from KO bladder detrusor is similar to that observed in WT, this would suggest that the detrusor retains the capacity to respond to nerve stimulation. This observation in the presence of deterioration of in vivo contractility would potentially indicate disruption of normal motor innervation. This seems a highly unlikely possibility due to the lack of any reports describing alteration of nerve function by miR-29a/b1. An altered response to carbachol and/or activation of purinergic receptors in tissue from KO bladders would be pursued by evaluating the relative abundance of muscarinic receptors and purinergic receptors, and use of receptor-specific antagonists in WT and KO bladders.

Aim 2. Role of Tissue-Specific Expression of miR-29a/b1 in Bladder Structure and Function Rationale These experiments will be performed to determine whether loss of miR-29a/b1 function in either the urothelium or detrusor is sufficient to recreate effects observed with global miR-29a/b1 KO.

Approach Our preliminary data indicate expression of miR-29a in the bladder is primarily limited to the urothelium and detrusor. These data further indicate that Col1a1 mRNA is most abundant in the *Lamina propria* and detrusor. Message for other components of the extracellular matrix are in both the urothelium and detrusor, but fibrosis is limited to the detrusor and *Lamina propria*. This raises an important question regarding the role of miR-29a/b1 signaling in the urothelium relative to changes in bladder structure and function, because it has a direct bearing on therapeutic approaches to prevention and treatment of bladder fibrosis.

Selective deletion of miR-29a/b1 from the urothelium or detrusor We will use a Cre-lox strategy to selectively eliminate miR-29a/b1 expression from the urothelium or detrusor to determine whether tissue-specific loss of miR-29a/b1 is sufficient to induce changes similar to those observed in global miR-29a/b1 KO mice. Mice will be generated that lack miR-29a/b1 expression in either the urothelium or detrusor. Mice are available that constitutive express Cre-recombinase under the control of the urothelium-specific uroplakin 2 (Upk2) promoter (Jackson Laboratories, Bar Harbor, ME; [B6(129)-Tg(Upk2-Cre)1Rkl/WghJ; stock #029281],109 and we have established a colony of these mice. We will purchase mice from Jackson Laboratories that express Cre-recombinase under the control of the Tbx18 promoter that is specific to the smooth muscle and mesenchymal tissues of the lower urinary tract (Tbx18-Cre, B6.CG-Tg(Tbx18-icre)3Fech/J).110 We have already obtained mice with loxP sequences inserted on the 5' and 3' side of the miR-29a/b1 gene (please see letter from Dr. Liston).111 These mice will be used to generate Upk2$^{Cre/Cre}$ miR-29a/b1$^{fl/fl}$ mice that constitutively lack miR-29a/b1 in the bladder urothelium and Tbx18$^{Cre/Cre}$ miR29a/b1$^{fl/fl}$ mice that constitutively lack miR-29a/b1 expression in the detrusor for these experiments. We will confirm the results of these breedings by genotyping and assessing expression of miR-29a in the urothelium or detrusor by in situ hybridization and RT-PCR for miR-29a using total RNA isolated from the urothelium and detrusor.

Histological and Functional Assays Bladder structure and function well be evaluated in experiments described in this Sub-Aim using the techniques previously described in Sub-Aims 1.1, 1.2, and 1.3.

Results and Alternative Approaches

We hypothesize that results obtained in mice lacking miR-29a/b1 expression in either the urothelium or detrusor will resemble those obtained with mice lacking systemic expression of miR-29a/b1 (KO). This would indicate translocation of miR-29a/b1 in a paracrine manner from the urothelium to the site of action in the *Lamina propria* or detrusor. Alternatively, results may demonstrate that location (i.e., urothelium vs. detrusor) of miR-29a/b1 expression is critical to the structural and functional effects of miR-29a/b1 in the bladder. Lack of effect of urothelium-specific deletion of miR-29a/b1 would indicate that either systemic miR-29a/b1 is sufficient to replace that normally generated by the urothelium, other tissues in the bladder (i.e., the detrusor) synthesize adequate quantities of miR-29a/b1, or that a combination of these processes maintains homeostasis. Similarly, if results obtained in mice deficient for miR-29a/b1 specifically in the detrusor fail to replicate those obtained in mice with global loss of miR-29a/b1 (KO) would suggest that systemic or urothelial synthesis is sufficient to compensate for loss of detrusor synthesis of miR-29a/b1. It is also possible that results in these mice will be an intermediate phenotype. If in situ hybridization and RT-PCR fail to confirm absence of miR-29a/b1 in the detrusor of Tbx18$^{Cre/Cre}$ miR29a/b1$^{fl/fl}$ mice, we will obtain mice that express tamoxifen-inducible Cre-recombinase under control of the smooth muscle-specific SM22 promoter (SM-CreERT2) to target deletion of miR-29a/b1 expression from the detrusor. Although this particular promoter is active in all smooth muscle, these mice were used to specifically study the effects of deletion of neuropilin 2 in the bladder.[112] These studies will help to clarify the relative importance of expression of mir-29a/b1 in the urothelium or detrusor in the overall function of miR-29a/b1 in the bladder. There appears to be limited expression of miR-29a in the *Lamina propria* of WT mice. However, if selective deletion of miR-29a/b1 in neither the urothelium or the detrusor provides results similar to those observed in global miR-29a/b1 mice, a third tissue-specific option is to cross Gli$^{tm3(cre/ERT2)Alj}$ mice to miR29a/b1$^{fl/fl}$ mice. The Gli$^{tm3(cre/ERT2)Alj}$ (stock #007913; Jackson Laboratories, Bar Harbor, ME) express Cre-recombinase under control of the Gli1 promoter when treated with tamoxifen, and these mice have been used to target cells within the bladder *Lamina propria*.[113]

Aim 3. Effect of miR-29a/b1 on Bladder Dysfunction and Structure Induced by Partial Bladder Outlet Obstruction Rationale These experiments will be performed to assess the capacity of miR-29a/b1 to prevent or reverse the effects of BOO on bladder structure and function.

Figure 12:
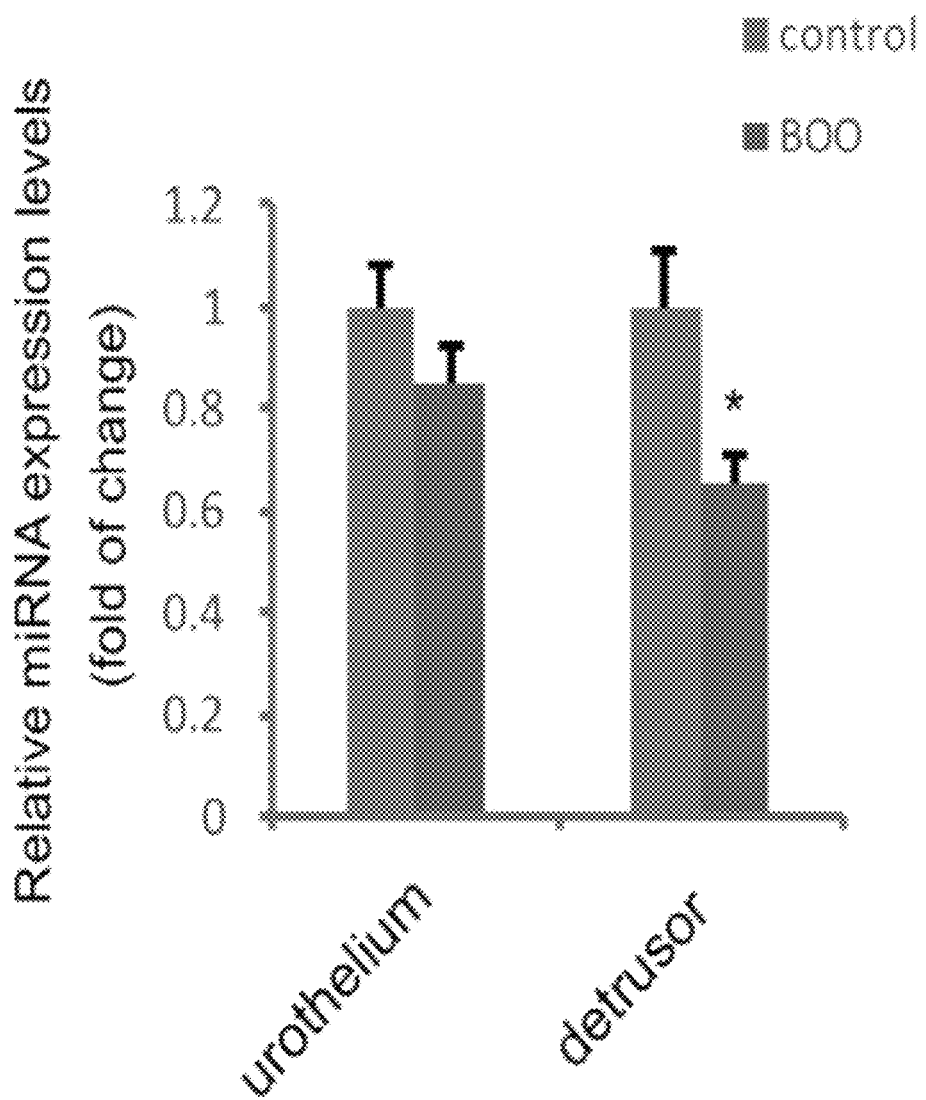
FIG. 12 is a bar graph showing that 10 days of BOO in male WT mice significantly decreased the abundance of miR-29a in the detrusor.
Figure 13A:
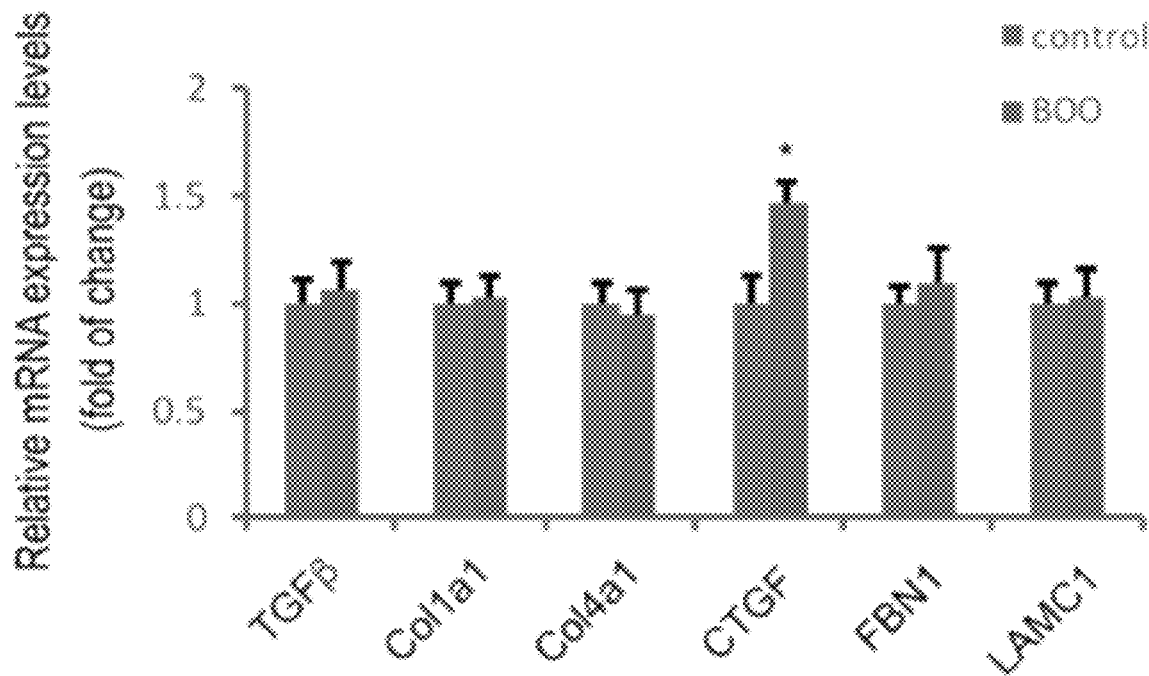
FIG. 13A is a bar graph showing that after 10 days of BOO in WT mice, CTGF mRNA was increased in the urothelium.
Figure 13B:
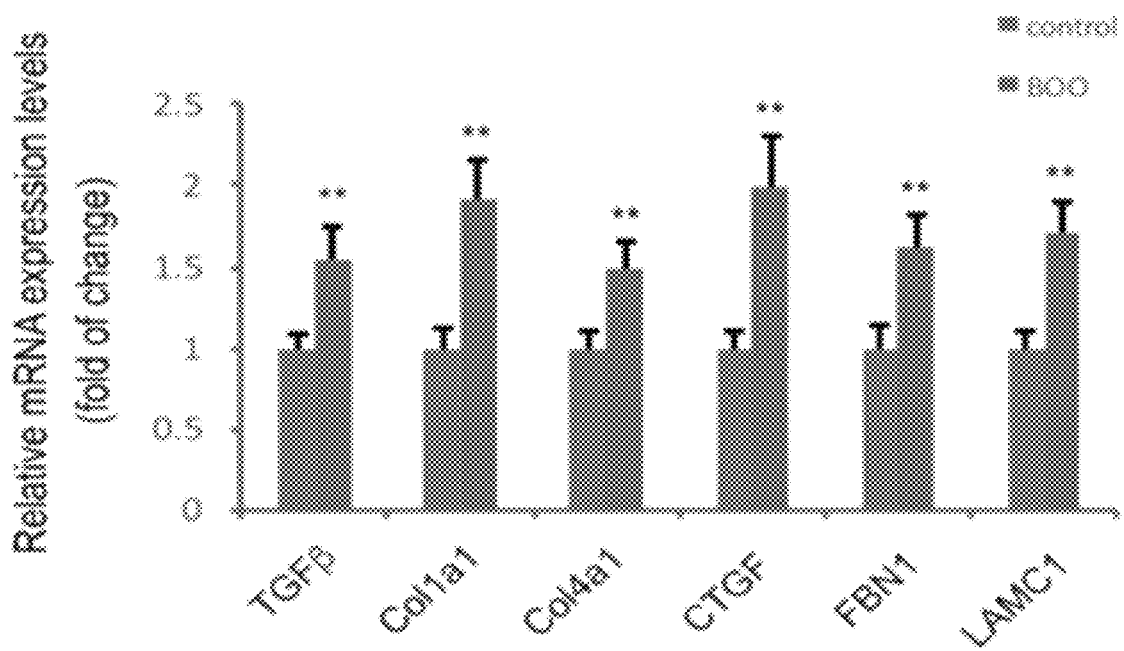
FIG. 13B is a bar graph showing that after 10 days of BOO in WT mice, message for TGFβ, Col1a1, Col4a1, connective tissue growth factor (CTGF), fibronectin (FBN1), and laminin (LAMC1) were all increased in the detrusor.
Figure 14A:
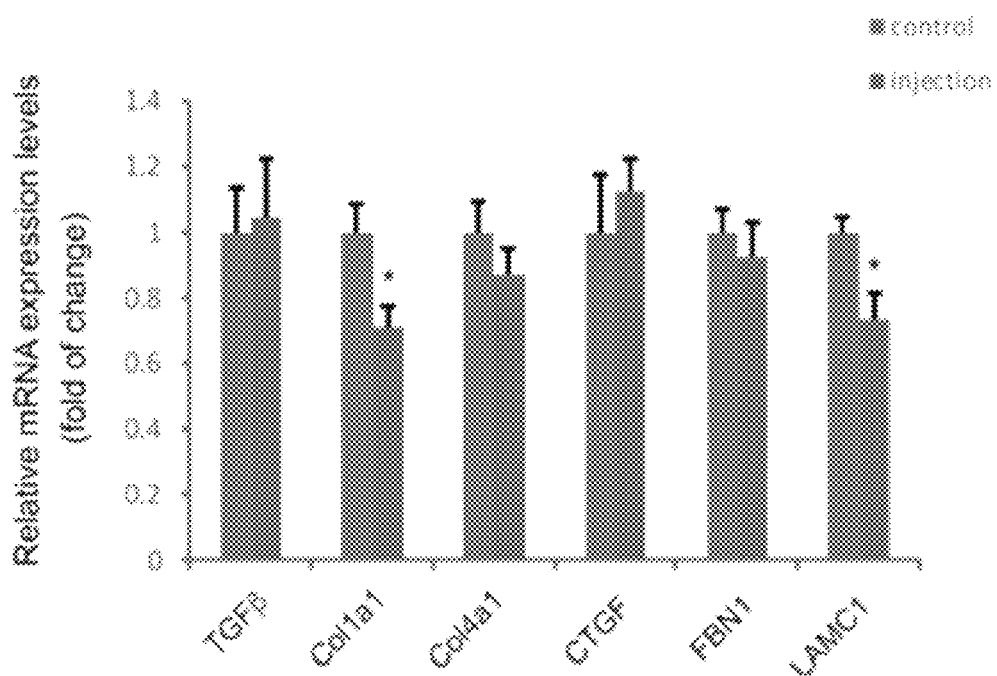
FIG. 14A is a bar graph showing treatment of mice with the Locked RNA™ miR-29a mimic (injection; Exiqon, Woburn, MA; 6 treatments at 25 µg/treatment given ip beginning 24 hr before creation of BOO, repeated on the day of surgery, and 2, 4, 6 and 8 days after surgery) resulted in decreased mRNA for Col1a1 and laminin in the urothelium when compared to vehicle-treated BOO controls after 10 days of obstruction.
Figure 14B:
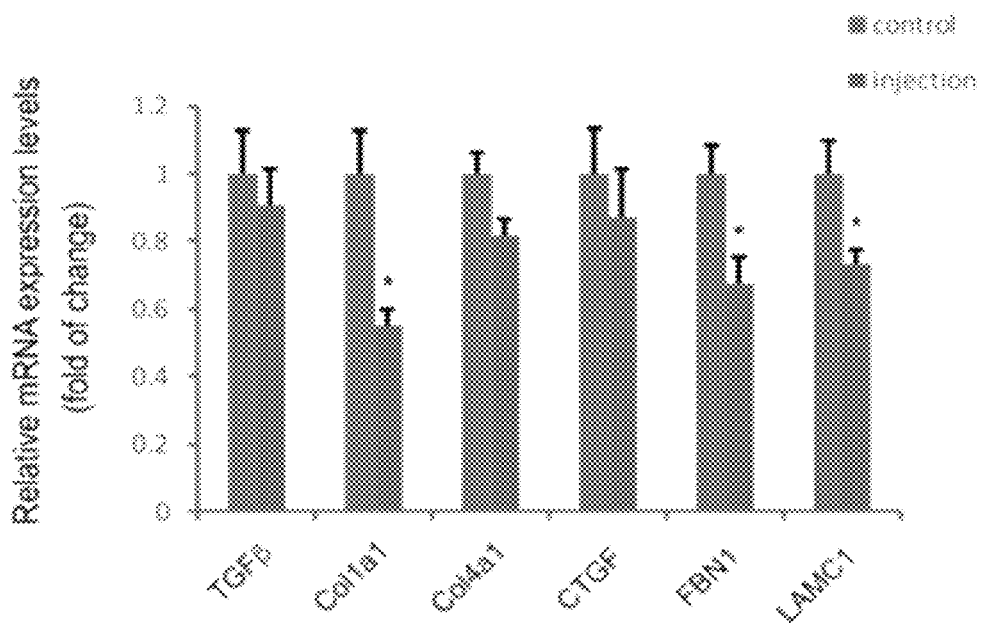
FIG. 14B is a bar graph showing that treatment of mice with the Locked RNA™ miR-29a mimic (injection; Exiqon, Woburn, MA; 6 treatments at 25 µg/treatment given ip beginning 24 hr before creation of BOO, repeated on the day of surgery, and 2, 4, 6 and 8 days after surgery) resulted in decreased message for col1a1, fibronectin, and laminin in the detrusor when compared to vehicle-treated BOO controls after 10 days of obstruction.

Approach The capacity of increased abundance of miR-29 to prevent or reverse fibrosis and improve organ function has been repeatedly demonstrated experimentally in organs other than the bladder. It has recently been reported that miR-29a/b1 plays a crucial role in maintenance of myocardial contractility.[76] We found that 10 days of BOO in male mice decreased abundance of miR-29a in the detrusor (FIG. 12), and increased abundance of mRNA for molecules associated with increased extracellular matrix in the detrusor with a more limited effect in the urothelium (FIG. 13). Systemic treatment of mice with miR-29a mimic decreased message for Col1a1, fibronectin, and laminin in the detrusor and decreased mRNA for Col1a1 and laminin in the urothelium when compared to BOO controls after 10 days of obstruction (FIG. 14). These results are consistent with observations in other organs in which overexpression of miR-29 prior to or after establishment of fibrosis prevented or reversed fibrosis and restored organ function in animal models of fibrosis in the lungs,[12, 13] liver,[10, 13, 17, 66] heart,[9] kidney,[16, 17] or uterus.[114] The therapeutic application of manipulation of miRNA and status of past and current clinical trials in humans has been recently reviewed.[115] This aim will address the therapeutic potential of miR-29 utilizing a well-established model of bladder fibrosis and dysfunction.

Creation of BOO Partial BOO will be created in male and female WT mice as previously described.[112, 116-118] Briefly, a caudal abdominal incision will be made in anesthetized mice to expose the bladder and proximal urethra. A length of polyethylene tubing (PE10; outer diameter 0.024 inches) is laid next to the urethra, a 6-0 silk suture is placed around the urethra and tubing, and the suture is tied snugly without compressing the tubing. The tubing is removed, and the abdomen is closed. Sham surgery will be performed in control animals by dissecting around the urethra, passing and removing the suture, and closing the abdomen.

Figure 15C:
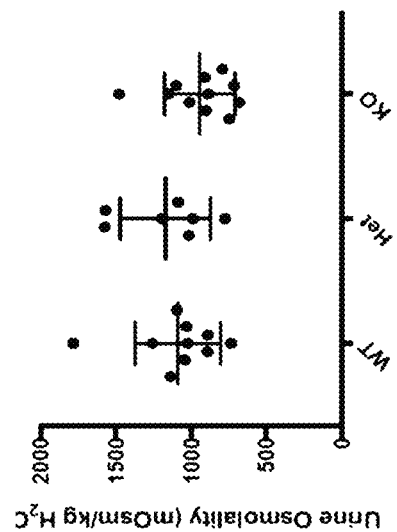
FIG. 15C is a graph showing that urine osmolality did not vary among wildtype, miR-29a+/− and miR-29a−/− mice at 10 weeks of age (n=10, 7, 11), indicating no differences in urine concentrating capacity of kidneys among genotypes.
Figure 15B:
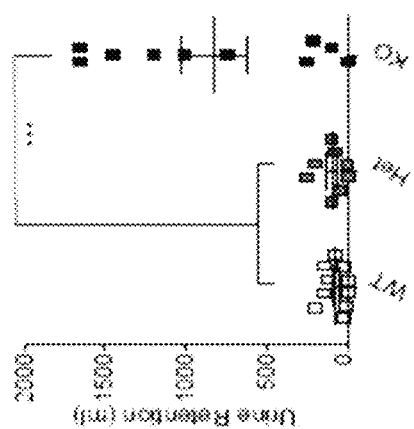
FIG. 15B is a graph showing recoverable urine volume from the bladders of wildtype, miR-29a+/− and miR-29a−/− mice at 10 weeks of age (n=10, 8, 10).

Increasing mIR-29a/bf in bladders of mice with BOO Adeno-associated virus 9 (AAV9) has shown tissue trophism for peripheral organs.[119-122] AAV9-miR-29b administered intranasally to mice increased epithelial expression of miR-29b and suppressed fibrosis.[123] Efficacy of AAV9 delivery of transgenes has also been shown to be durable, with effects lasting at least 18 months after subretinal delivery of retinitis pigmentosa GTPAse regulator in mice.[122] The primary receptor for AAV9 carries a terminal sialic acid that can be removed with neuraminidase to expose galactose, the preferred binding molecule for AAV9.[124,125] Primary murine urothelial cells were cultured in vitro in the presence of neuraminidase (50 mU/ml for 1 hour) and then exposed to AAV9-mCherry ($10^{10}$ vector genomes or VG) for 72 hours. Expression of mCherry was observed as expected after 72 hours of culture (FIG. 15). Control animals (BOO and sham operated) will receive AAV9 expressing mCherry under control of the cytomegalovirus promoter. The goal of these experiments is to increase expression of miR-29a/b1 in the bladder wall to determine the efficacy of this approach to suppress fibrosis and abnormal function of bladders subjected to BOO. We will evaluate both intravesical and intramural delivery of the AAV9-miR-29b vector. Intravesical delivery, if effective, would be easier and less invasive and traumatic than intramural injection of the AAV9-miR-29b vector into the bladder wall. However, intramural injection of the vector could be performed in patients during cystoscopy. We have developed a technique for transurethral passage of a catheter into bladders of male mice without perforating the urethral wall. Male and Female mice will be anesthetized, a urethral catheter will be passed, the bladder will be emptied, and 50 mU of neuraminidase (9001-67-6, Sigma-Aldrich, St. Louis, MO) AAV9 will be instilled intravesically (50 µl volume). One hour later, AAV9-miR-29a/b1 ($5 \times 10^{11}$ VG, 50 µl) will be instilled into the bladder, and mice will remain anesthetized an additional hour before removing the catheter. Male and female mice will be anesthetized, the bladder will be exposed via an incision, and AAV9-miR-29a/b1 or AAV9-mCherry (total viral dose will be $5 \times 10^{11}$ VG) will be injected into 4-5 sites of the bladder wall (20 µl/site). Bladder function and structure will be studied 10 days, 3 weeks, and 6 weeks after BOO surgery.

Histological and Functional Assays Bladder structure and function well be evaluated in experiments described in this Sub-Aim using the techniques previously described in Sub-Aims 1.1, 1.2, and 1.3.

Results and Alternative Approaches

We anticipate that increased miR-29a/b1 expression induced by AAV9 delivery to the bladder will prevent or reverse fibrosis in response to BOO in WT mice. This would be of significant translational importance, particularly if intravesical delivery of AAV9 can achieve this. If intravesical delivery of AAV9 proves ineffective, we will consider instilling 0.1% n-dodecyl-β-D-maltoside (DDM; D4641, Sigma-Aldrich, St. Louis, MO) for 5 minutes prior to instillation of neuraminidase. This is a mild detergent that has been demonstrated to increase trans-urothelial uptake of viral vectors.[126] If neither intravesical or intramural delivery of AAV9 carrying miR-29a/b1 reverses fibrosis resulting from BOO, consideration will be given to systemic delivery by intraperitoneal injection of miR-29a oligonucleotide mimics, as done in preliminary studies. Systemic instillation of miR-29 has been shown to be an effective therapeutic approach in preventing or reversing fibrosis in several organs.[9-13,66] A recent breakthrough in generation of microRNA mimics was to use internally segmented interfering RNA.[127] Efficacy of systemic administration of miR-29a oligonucleotide mimics would provide proof of concept. However, we would prefer to use bladder-specific delivery of miR-29a/b1 to minimize the potential for off-target effects.

Statistical Analysis

There will be at least 8 separate replicates for each factor studied for a specific genotype or treatment. 8 replicates provides 95% confidence that observed differences are correct. Data generated by multiple observations in $$n/2 = \frac{\sigma^2 \times (Z_{\alpha/2} + Z_\beta)^2}{(\mu H_A - \mu H_O)^2}$$

more than one group are typically analyzed by two-way ANOVA followed by a post hoc test. Group size is determined by performing a power calculation using the following formula:

In which n=group size; $\sigma^2$=population variance; Z=ideal value for normal distribution (typically obtained from a table); α/2=the desire p value (typically 0.05) divided by 2; β=1-power (typically 0.8); and $\mu H_A - \mu H_O$=the difference between observed population distribution and hypothesized distribution (often considered 0). A type I error occurs when $H_O$ is rejected when $H_O$ is true, and α reflects the probability of making type I error. When $H_O$ is true, power=α. A type II error occurs when $H_O$ is accepted but $H_O$ is actually false, and β reflects the probability of making a type II error. When $H_O$ is false, power=1-β. Thus, when we insert numbers from data sets generated in our experiments, we find that 8 replicates avoids either a type I or type II error. Direct comparison of functional data, RNA expression, or protein abundance between 2 groups will be performed using Student's t-test. Comparisons over time or within groups will be performed by analysis of variance (ANOVA). Comparison of multiple groups or multiple measurements will performed using ANOVA pre hoc and the Scheffe F to determine post hoc significance. Significance will be set at 95% confidence limits.

Example 2: Injectable Compostions Containing an Mir-29 Mimic

To develop an injectable composition containing an miR-29 mimic, the following experiments were conducted.

Additional details regarding these experiments are provided in Appendix B, incorporated by reference herein in its entirety.

Introduction and Objective: MicroRNAs (miRNA) are short (19-25 nucleotides), non-coding RNA sequences that bind to the 3' untranslated region of various messenger RNA (mRNA), accelerating mRNA degradation or preventing translation of the encoded protein. MicroRNA-29 or miR-29 suppresses translation of genes related to extracellular matrix (ECM) formation, particularly various collagens, collagen cross-linking elements, and enzymes that regulate post-translational modification of the ECM proteins. Dysregulation of ECM formation results in fibrosis. A recent study comprehensively investigated miRNA abundance and signaling in bladder biopsies from patients with bladder outlet obstruction and found significant increases or decreases in multiple miRNAs, but specifically reported a decrease in miR-29.

Methods: Bladder outlet obstruction (BOO) was created in male C57BL/6 mice, and mice were sacrificed 10 days later. Abundance of miR-29a in the urothelium and detrusor was determined, as was abundance of mRNA encoding for transforming growth factor-β (TGFβ), collagen 1α1 (col1a1), collagen 4a1 (col 4a1), connective tissue growth factor (CTGF), fibronectin-1 (FBN1), and laminin C1 (LAM). In two other groups, mice were injected with miR-29a mimic or vehicle (6 treatments at 25 μg/treatment given ip beginning 24 hr before creation of BOO, repeated on the day of surgery, and 2, 4, 6, and 8 days after surgery) and sacrificed 10 days after creation of BOO.

Results: The abundance of miR-29a was decreased in the detrusor, but not the urothelium, after 10 days of BOO (FIG. 12). mRNA encoding for TGFβ, col1a1, col 4a1, FBN1, and LAM were all significantly increased in the detrusor (FIG. 14) of mice with BOO compared to sham-operated controls.

Message for CTGF was increased in both the detrusor and urothelium. Injection of mice with miR-29a mimic decreased message for col 1a1 and LAM in both the urothelium and detrusor, as well as message for FBN1 in the detrusor, compared to BOO mice treated with vehicle.

Figure 15A:
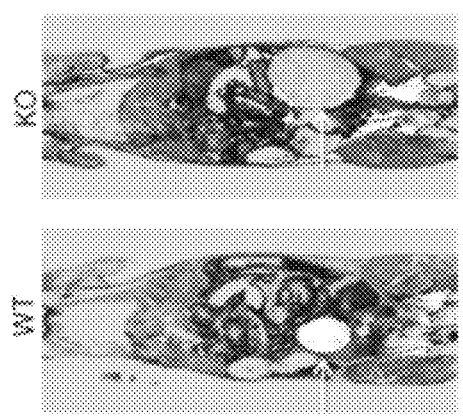
FIG. 15A contains representative MRI images of wildtype and miR-29a−/− mice at 10 weeks of age, with the bladder indicated by the white arrow.

FIG. 15A shows representative MRI images of wildtype and miR-29a-/- mice at 10 weeks of age, with the bladder indicated by the white arrow. FIG. 16B shows recoverable urine volume from the bladders of wildtype, miR-29a+/- and miR-29a-/- mice at 10 weeks of age (n=10, 8, 10). FIG. 15C shows that urine osmolality did not vary among wildtype, miR-29a+/- and miR-29a-/- mice at 10 weeks of age (n=10, 7, 11), indicating no differences in urine concentrating capacity of kidneys among genotypes.

Figure 16:
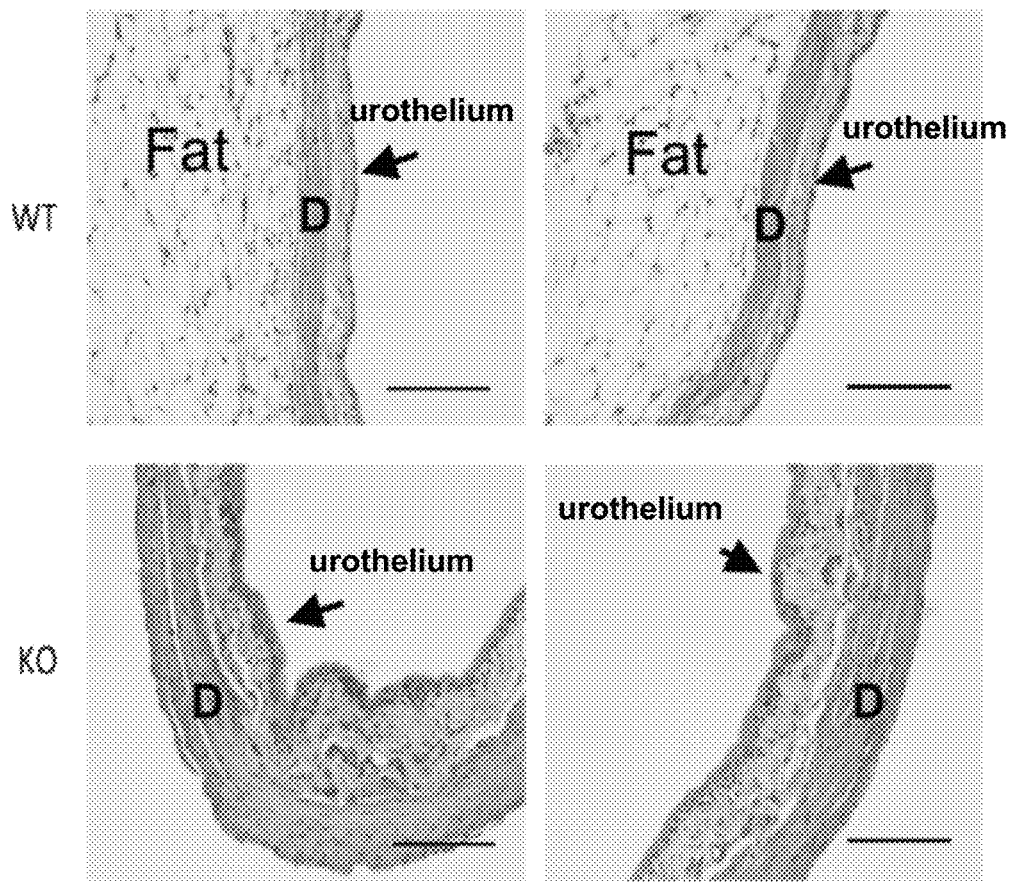
FIG. 16 contains a series of microscope images showing H&E staining of bladders from 10 week old female wildtype (WT) and miR-29 knock out (KO) mice. Arrows point to urothelium. D=detrusor. Note increased thickness of detrusor and submucosa in miR-29 KO mice at this age. Bars=100 µm.

FIG. 16 shows H&E staining images of bladders from 10 week old female wild-type (WT) and miR-29 knock out (KO) mice. Arrows point to urothelium. D=detrusor. Note increased thickness of detrusor and submucosa in miR-29 KO mice at this age. Bars=100 μm.

Conclusions: These results indicate: 1. abundance of miR-29a is decreased by BOO; and 2. miR-29a has the capacity to decrease message for components of fibrosis in the presence of BOO. Further research is required, but these experiments support consideration of miR-29a as a potential therapy to prevent or treat BOO-associated bladder fibrosis.

MiR-29 Mimics and Uses Thereof for Treatment of Bladder Obstructive Diseases

Abstract: The present disclosure describes chemically modified synthetic miR-29 mimic molecules and pharmaceutical composition comprising miR-29 mimic molecules and carrier molecules and their use in reversing bladder obstructive diseases.

Background

Bladder fibrosis is relatively common in patients subsequent to partial bladder outlet obstruction (BOO),[1] neurogenic disorders,[2] radiation therapy of the lower abdomen,[3] chronic inflammation,[4] or as a natural effect of aging.[5] Furthermore, fibrosis often persists beyond resolution of the inciting factor(s), particularly in pediatric patients, and lack of effective strategies to reduce bladder fibrosis remains a significant therapeutic gap.[6]

MicroRNAs are single-stranded, non-coding RNA molecules 19-25 nucleotides in length generated from endogenous hairpin-shaped transcripts.[7] MicroRNAs bind to specific target mRNAs, and either repress translation of mRNA or cause destabilization of mRNA thereby accelerating mRNA degradation.[8] The microRNA-29 (miR-29) family suppresses translation of genes that promote expression of many components of the extracellular matrix, including 20 isoforms of collagen, laminin γ1, fibrillin 1, elastin, and integrin β1.[9-12] Compelling evidence has been reported that miR-29 is decreased in bladders of patients with BOO[13] and in rats with experimentally-created BOO.[14,15]

Description

The present disclosure is based, at least in part, on the discovery that administration of miR-29 mimics into the experimental BOO mouse can reverse bladder fibrosis based upon gene expression program.

Experimental BOO in rodents caused bladders to pass through predictable phases of inflammation and muscle hypertrophy, ending in deterioration characterized by fibrosis and decreased contractility and compliance,[1,16] a progression also described in BOO of human bladders.[17] Prolonged retention of urine associated with BOO results in increased extracellular matrix content comprised of collagen and elastic fibers, as well as causing degeneration of muscle fibers.[18-20]

As described herein, administration of miR-29a mimic to BOO mice decreased gene expression levels for Col1a1, fibronectin, and laminin in the detrusor and decreased gene expression levels for Col1a1 and laminin in the urothelium when compared to BOO controls after 10 days of obstruction.

The present disclosure provides for the identification of effective miR-29 mimic molecules; methods for conjugating miR-29 mimics with carrier molecules; dose and duration for I.V. injection route of miR-29 mimic molecules in mice; after injection of miR-29 mimics, data shows reduction in bladder fibrotic program.

MIR-29 Genes

The miR-29 gene family consists of three members (miR-29a, miR-29b and miR-29c) which are encoded by two distinct genomic loci (a/b1 and b2/c) in both human and rodent genomes[21]. The miR-29a and b1 genes are clustered into the a/b1 locus and share the same promoter, while miR-29b2 and c genes are primed from the b2/c locus using a single promoter. As all members have the same seed binding sequence, they all bind to the same set of target genes. The human and rodent miR-29 gene sequences are identical.

```
Nucleotide sequence
MiR-29a
                                       (SEQ ID NO: 1)
UAGCACCAUCUGAAAUCGGUUA MiR-29b
                                       (SEQ ID NO: 2)
UAGCACCAUUUGAAAUCAGUGUU MiR-29c
                                       (SEQ ID NO: 3)
UAGCACCAUUUGAAAUCGGUUA MiR-29 mimics
Working strand sequence:
                                       (SEQ ID NO: 4)
UAGCACCAUCUGAAAUCGGUUUU Passenger strand sequence:
                                       (SEQ ID NO: 5)
AACCGAUUUCuunUGGUGCUAUU
```

The Passenger strand are modified:
1, contain 2-O-methylation modification to increase stability
2, cholesterol is conjugated to 3'-end to enhance cellular uptake Carrier Molecule Polyethylenimine, branched, Mw: 25 kDa., CAS No: 9002-98-6, Linear formula: H(NHCH2CH2)nNH2.

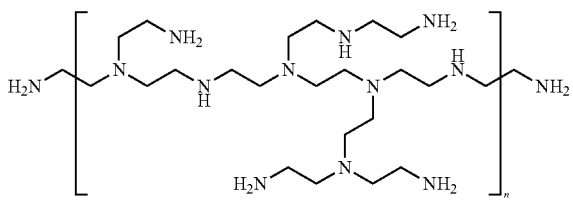

Conjugation

Polyethylenimine and miR-29 mimic are mixed at the N/P ratio of 0.8 (referring to the nitrogens of the polyethylenimine and the phosphate groups of the nucleic acid). The polyplexes are dissolved in 0.5% glucose solution and administered to animals.

Administration Route, Dosage and Duration

MiR-29 mimics are injected via IP at 25 μg/20 g mouse beginning 24 hr before creation of BOO, repeated on the day of surgery, and 2, 4, 6 and 8 days after surgery

What is claimed is:

1. A composition for the treatment of bladder fibrosis in a patient in need, the composition comprising an miR-29 mimic, the miR-29 mimic comprising a working RNA strand comprising the nucleotide sequence UAGCACCAUCUGAAAUCGGUUUU (SEQ ID NO 4) and a passenger RNA strand comprising the nucleotide sequence: AACCGAUUUCuuuUGGUGCUAUU (SEQ ID NO 5).

2. The composition of claim 1, wherein the passenger RNA strand further comprises a 2'-O-methylation modification to increase stability and a cholesterol conjugated to a 3'-end of the passenger RNA strand to enhance cellular uptake.

3. The composition of claim 2, further comprising a carrier molecule.

4. The composition of claim 3, wherein the carrier molecule comprises branched polyethylenimine.

5. The composition of claim 4, further comprising an N/P ratio of 0.8, where N denotes the nitrogens of the polyethylenimine and P denotes the phosphate groups of the working and passenger RNA strands.

6. The composition of claim 5, wherein the polyethylenimine, the working RNA strand, and the passenger RNA strand form a polyplex.

7. The composition of claim 6, wherein the polyplex is dissolved in a glucose solution.

8. The composition of claim 7, wherein the glucose solution is a 0.5% glucose solution.

9. A method of reducing or reversing bladder fibrosis in a patient in need, the method comprising administering an effective amount of a composition, the composition comprising an miR-29 mimic, the miR-29 mimic comprising a working RNA strand comprising the nucleotide sequence UAGCACCAUCUGAAAUCGGUUUU (SEQ ID NO 4) and a passenger RNA strand comprising the nucleotide sequence: AACCGAUUUCuuuUGGUGCUAUU (SEQ ID NO 5).

10. The method of claim 9, wherein the passenger RNA strand further comprises a 2'-O-methylation modification to increase stability and a cholesterol conjugated to a 3'-end of the passenger RNA strand to enhance cellular uptake.

11. The method of claim 10, wherein the composition further comprises a carrier molecule.

12. The method of claim 11, wherein the carrier molecule comprises branched polyethylenimine.

13. The method of claim 12, the composition further comprises an N/P ratio of 0.8, where N denotes the nitrogens of the polyethylenimine and P denotes the phosphate groups of the working and passenger RNA strands.

14. The method of claim 13, wherein the polyethylenimine, the working RNA strand, and the passenger RNA strand form a polyplex.

15. The method of claim 14, wherein the polyplex is dissolved in a glucose solution.

16. The method of claim 15, wherein the glucose solution is a 0.5% glucose solution.

* * * * *